US008476083B1

(12) United States Patent
Algar et al.

(10) Patent No.: US 8,476,083 B1
(45) Date of Patent: Jul. 2, 2013

(54) SPECTRO-TEMPORAL OPTICAL ENCODING OF INFORMATION USING A TIME-GATED FLUORESCENCE RESONANCE TRANSFER (FRET)

(75) Inventors: W. Russ Algar, Alexandria, VA (US); Niko Hildebrandt, Orsay (FR); Alan L Huston, Aldie, VA (US); Igor L. Medintz, Springfield, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/475,177

(22) Filed: May 18, 2012

(51) Int. Cl.
*G01N 33/551* (2006.01)
*G01N 21/76* (2006.01)
*C09K 11/06* (2006.01)
*G01N 33/53* (2006.01)
*G01N 21/64* (2006.01)

(52) U.S. Cl.
USPC ...................... 436/524; 250/486.1; 250/484.2; 977/774; 977/896; 977/950; 422/82.05; 422/82.08; 435/4; 435/6.1; 435/7.1; 252/301.16; 436/172

(58) Field of Classification Search
None
See application file for complete search history.

(56) References Cited

U.S. PATENT DOCUMENTS

| | | | |
|---|---|---|---|
| 2006/0148104 A1* | 7/2006 | Marini et al. | 436/524 |
| 2008/0087843 A1* | 4/2008 | Medintz et al. | 250/484.2 |
| 2008/0213780 A1* | 9/2008 | Butlin et al. | 435/6 |
| 2009/0162861 A1* | 6/2009 | Mathis et al. | 435/6 |
| 2011/0089241 A1* | 4/2011 | Medintz et al. | 235/462.04 |

* cited by examiner

*Primary Examiner* — Neil N Turk
(74) *Attorney, Agent, or Firm* — Amy Ressing; Roy Roberts

(57) ABSTRACT

Described herein is a time-gated, two-step FRET relay effective to provide temporal transference of a prompt FRET pathway, or provide spectro-temporal encoding analytical signals and other information. A FRET relay assembly includes a long lifetime FRET donor (for example, a lanthanide complex), a semiconductor quantum dot (QD) configured as an intermediate acceptor/donor in FRET, and a fluorescent dye configured as a terminal FRET acceptor, wherein the long lifetime FRET donor has an excited state lifetime of at least one microsecond and the QD and fluorescent dye each have excited state lifetimes of less than 100 nanoseconds.

7 Claims, 8 Drawing Sheets

SEQUENCE LISTING

```
<160> NUMBER OF SEQ ID NOS: 7

<210> SEQ ID NO 1
<211> LENGTH: 29
<212> TYPE: PRT
<213> ORGANISM: Artificial Sequence
<220> FEATURE:
<223> OTHER INFORMATION: synthetic construct

<400> SEQUENCE: 1

Cys Ser Thr Arg Ile Asp Glu Ala Asn Gln Arg Ala Thr Lys Leu Pro
1               5                   10                  15

Pro Pro Pro Pro Pro Pro Ser His His His His His His
            20                  25

<210> SEQ ID NO 2
<211> LENGTH: 15
<212> TYPE: PRT
<213> ORGANISM: Artificial Sequence
<220> FEATURE:
<223> OTHER INFORMATION: synthetic construct

<400> SEQUENCE: 2
```

```
Gly Ser Gly Ala Ala Ala Gly Leu Ser His His His His His
1               5                   10                  15

<210> SEQ ID NO 3
<211> LENGTH: 18
<212> TYPE: DNA
<213> ORGANISM: Artificial Sequence
<220> FEATURE:
<223> OTHER INFORMATION: synthetic construct

<400> SEQUENCE: 3
ttagttctgt tataacaa                                                 18

<210> SEQ ID NO 4
<211> LENGTH: 16
<212> TYPE: PRT
<213> ORGANISM: Artificial Sequence
<220> FEATURE:
<223> OTHER INFORMATION: synthetic construct

<400> SEQUENCE: 4

Cys Gly Ser Gly Ala Ala Ala Gly Leu Ser His His His His His
1               5                   10                  15

<210> SEQ ID NO 5
<211> LENGTH: 18
<212> TYPE: DNA
<213> ORGANISM: Artificial Sequence
<220> FEATURE:
<223> OTHER INFORMATION: synthetic construct

<400> SEQUENCE: 5
aatcaagaca atattgtt                                                 18

<210> SEQ ID NO 6
<211> LENGTH: 18
<212> TYPE: DNA
<213> ORGANISM: Artificial Sequence
<220> FEATURE:
<223> OTHER INFORMATION: synthetic construct

<400> SEQUENCE: 6
caacatccta attgactt                                                 18

<210> SEQ ID NO 7
<211> LENGTH: 18
<212> TYPE: DNA
<213> ORGANISM: Artificial Sequence
<220> FEATURE:
<223> OTHER INFORMATION: synthetic construct

<400> SEQUENCE: 7
gttgtaggat taactgaa                                                 18
```

SPECTRO-TEMPORAL OPTICAL ENCODING OF INFORMATION USING A TIME-GATED FLUORESCENCE RESONANCE TRANSFER (FRET)

BACKGROUND

The introduction of luminescent semiconductor nanocrystals or quantum dots (QDs) to biology has provided researchers with novel fluorescent tools for potentially achieving advances in imaging and sensing. See, for example, U.S. Patent Application Publication Nos. 2008/0087843 and 2011/0089241, each of which is incorporated herein by reference. In particular, QDs have been widely adopted as either donors or acceptors in Förster resonance energy transfer (FRET)-based assays and biosensors.

FRET has been used in a wide variety of applications, including: static distance measurements within or between (bio)molecules (i.e. FRET as a "spectroscopic ruler" between ~1-10 nm); dynamic observation of changes in biomolecular conformation; diagnostic constructs that use changes between FRET "on" (high efficiency) and "off" (low efficiency) states to detect chemical/biological analytes; and light harvesting/photonic wires. In spectroscopic ruler contexts, FRET is generally implemented in its simplest configuration, which comprises a single donor luminophore and single acceptor chromophore. The FRET efficiency can be used to derive the donor-acceptor separation distance and is almost always measured on the basis of quenching of the donor luminescence intensity or decrease in the donor excited state lifetime. When the acceptor chromophore is also fluorescent, the ratio of acceptor and donor luminescence intensities can be a useful qualitative or quantitative measure. Diagnostic probes (for example, molecular beacons, Scorpion primers, or TaqMan probes) also predominately utilize discrete donor-acceptor pairs. Multi-step FRET relays have been described previously, using only prompt (nanosecond scale) fluorescence. The primary purpose has been to extend the net range of FRET or serve as a photonic wire.

Described herein is a time-gated, two-step FRET relay effective to provide temporal transference of a prompt FRET pathway, or provide spectro-temporal encoding.

BRIEF SUMMARY

In one embodiment, a FRET relay assembly includes a long lifetime FRET donor, a semiconductor quantum dot (QD) configured as an intermediate acceptor/donor in FRET, and a fluorescent dye configured as a terminal FRET acceptor, wherein the long lifetime FRET donor has an excited state lifetime of at least one microsecond and the QD and fluorescent dye each have excited state lifetimes of less than 100 nanoseconds.

BRIEF DESCRIPTION OF THE DRAWINGS

FIG. 1A (i) shows time-gated FRET sensitization of QD photoluminescence (PL) via $FRET_1$. Both the Tb and QD are initially excited by a flash of UV light; however, the QD relaxes to its ground state after a suitable microsecond delay (time gate) and becomes a good FRET acceptor for a proximal long-lifetime Tb donor. FIG. 1A (ii) shows time-gated sensitization of A647 PL via $FRET_1$ and $FRET_2$. The co-assembly of a fluorescent dye, A647, with the Tb around a QD permits a two-step energy transfer relay with the QD as an intermediary. In FIG. 1B, the QD is able to serve as a nanoscaffold for the controlled assembly of biomolecules labeled with Tb and A647.

FIG. 3C shows non-gated (~0 μs) and time-gated (55 μs) PL excitation spectra for QD, PEP B-Tb, and conjugates collected at Tb (490 nm) and QD (625 nm) PL emission wavelengths.

FIG. 6A shows times courses of trypsin proteolytic activity using (PEP B-Tb)$_{10}$-QD-(PEP A-A647)$_3$ assemblies. The time-gated (i) QD and (ii) A647 PL were monitored and converted to (iii) FRET efficiency. Dashed lines represent tangents drawn to calculate the initial rate. (iv) The initial rate of change of FRET efficiency was proportional to the trypsin concentration. FIG. 6B(i) shows PL spectra for the non-gated calibration of TGT A-A647 hybridization using QD-(PRB A)$_{15}$ assemblies. The inset shows the FRET efficiency and A647/QD PL ratio as a function of TGT A-A647 per QD. FIG. 6B(ii) shows time-gated sensing of TGT A-A647 using (PEP B-Tb)$_{10}$-QD-(PRB A)$_{12}$ assemblies. The inset shows the FRET efficiency and A647/QD PL ratio as a function of TGT A-A647 concentration. Note: the corresponding TGT A-A647 added is given in equivalents in (i) and concentration in (ii).

DETAILED DESCRIPTION

Definitions

Figure 1:
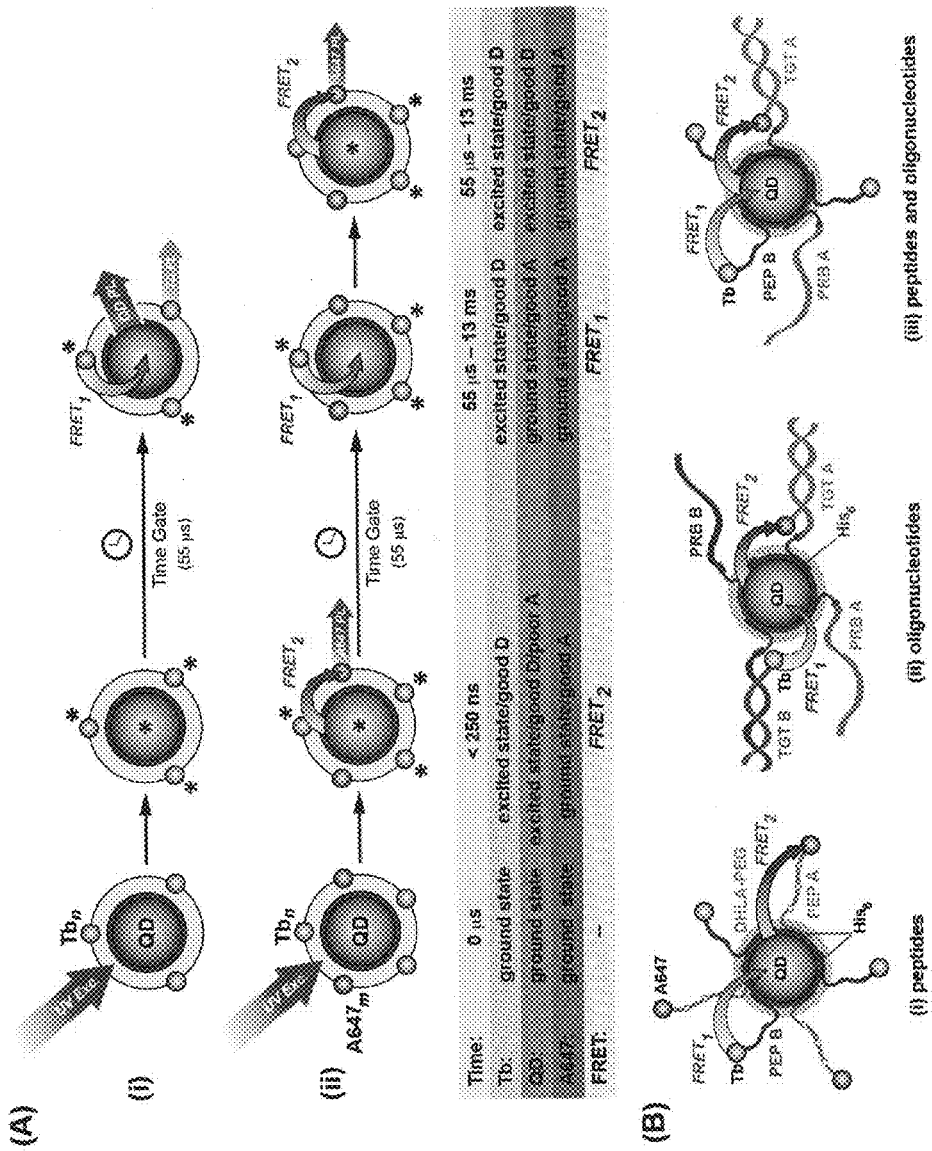
FIG. 1 shows exemplary embodiments illustrating the concept of the time-gated, two-step FRET relay.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

FRET refers to Fluorescence Resonance Energy Transfer, also termed Förster Resonance Energy Transfer.

The term "quantum dot" or "QD" as used herein refers to an inorganic semiconductor crystallite of about 1 nm or more and about 1000 nm or less in diameter or any integer or fraction of an integer therebetween, preferably at least about 2 nm and about 50 nm or less in diameter or any integer or fraction of an integer therebetween, more preferably at least about 2 nm and about 20 nm or less in diameter (for example about 2, 3, 4, 5, 6, 7, 8, 9, 10, 11, 12, 13, 14, 15, 16, 17, 18, 19, or 20 nm). QDs are characterized by their substantially uniform nanometer size, frequently exhibiting approximately a 10% to 15% polydispersion or range in size. A QD is capable of emitting electromagnetic radiation upon excitation (i.e., the QD is photoluminescent) and includes a "core" of one or more first semiconductor materials, and may be surrounded by a "shell" of a second semiconductor material. A QD core surrounded by a semiconductor shell is referred to as a "core/shell" QD. The surrounding "shell" material will preferably have a bandgap energy that is larger than the bandgap energy of the core material and may be chosen to have an atomic spacing close to that of the "core" substrate.

The core and/or the shell can be a semiconductor material including, but not limited to, those of the groups II-VI (ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, PbS, PbSe, and an alloy or a mixture thereof. Preferred shell materials include ZnS.

A QD is optionally surrounded by a "coat" of an organic capping agent. The organic capping agent may be any number of materials, but has an affinity for the QD surface. The coat can be used to convey solubility, e.g., the ability to disperse a coated QD homogeneously into a chosen solvent, functionality, binding properties, or the like. In addition, the coat can be used to tailor the optical properties of the QD. In general, the capping agent can be an isolated organic molecule, a polymer (or a monomer for a polymerization reaction), an inorganic complex, or an extended crystalline or amorphous structure. The two most common strategies for imparting aqueous solubility are the use of bifunctional ligand coatings and bifunctional polymer coatings. The former coordinate to the QD surface through a chemical function (e.g., thiol, imidazole) and replace the native hydrophobic ligands; the latter have pendant alkyl chains that interdigitate with the native ligands via hydrophobic interactions. In both cases, a second and polar chemical function—such as a carboxylate, amine, or poly(ethylene glycol) (PEG) chain—mediates aqueous solubility. Mixtures of different ligands and the use of copolymers enable the modification of QDs with multiple functional groups. Ligand coatings are advantageous in that more compact QDs are obtained; however, polymer coated QDs tend to have superior brightness and photostability. Standard bioconjugate techniques, such as carbodiimide coupling, are widely used with both ligand and polymer stabilized QDs. Ligand coatings have also frequently enabled the preparation of bioconjugates through self-assembly driven by coordination to the QD surface. Quantum dots herein include those having a simple core with or without a coat, as well as optionally coated core/shell QDs.

Description

As detailed herein, QDs can function in a simultaneous role as acceptors and donors within time-gated FRET relays. Aspects are described in Algar et al., *J. Am. Chem. Soc.* (2012) 134: 1876-1891, incorporated herein by reference along with its Supplemental Material.

The use of a two-step FRET relay serves to encode information having both a spectral and temporal dimensionality. This is achieved by assembling a configuration with an initial donor luminophore that has an excited state lifetime much longer (>10 μs) than both the intermediary acceptor/donor and terminal acceptor luminophores in the relay (<100 ns). Further, the two FRET steps are designed to be coupled but function approximately independently and resolvable from one another.

The technique described herein provides two novel attributes: (1) The FRET pathway from the QD to the fluorescent dye (termed $FRET_2$), which would normally only be observable within a time-gated window ~0-250 ns after optical excitation, can be shifted and extended into an observation window of at least 55-1055 μs, via the FRET pathway from the long lifetime FRET donor to the QD (termed $FRET_1$). Significantly longer timescales should be achievable in view of the Tb excited state lifetime of greater than one millisecond. (2) Spectral measurement of the FRET relay configuration in both the 0-250 ns and 55-1055 μs observation windows after excitation enables resolution of the $FRET_1$ and $FRET_2$ processes.

In the embodiment illustrated schematically in FIG. 1, a central CdSe/ZnS QD (~50 ns lifetime) serves as a scaffold for the co-assembly of initial donors and terminal acceptors, and also as the intermediary acceptor/donor to create a FRET relay. The QDs are made water soluble using a dithiolated poly(ethylene glycol) ligand that binds the QD. The initial donor is selected to be a luminescent $Tb^{3+}$ complex (Tb) (~2.5 ms lifetime), while the terminal acceptor is selected to be Alexa Fluor 647 (A647), a fluorescent dye (~1 ns lifetime). The FRET relay assembly may be interrogated using a commercial fluorescence plate reader capable of flash/pulsed excitation and spectral acquisition with time-gating.

Within the exemplary FRET relay, the QD served as an intermediate acceptor/donor, where: (1) an excited-state Tb donor transferred energy to the ground-state QD following a suitable microsecond delay; and (2) the QD subsequently transferred that energy to an A647 acceptor. A photophysical analysis was undertaken for each step of the FRET relay. The assembly of increasing ratios of Tb per QD was found to linearly increase the magnitude of the FRET-sensitized time-gated QD photoluminescence intensity. The Tb was found to sensitize the subsequent QD-A647 donor-acceptor FRET-pair without significantly affecting the intrinsic energy transfer efficiency within the second step in the relay. The utility of incorporating QDs into this type of time-gated energy transfer configuration was demonstrated in prototypical bioassays for monitoring protease activity and nucleic acid hybridization; the latter included a dual target format where each orthogonal FRET step transduced a separate binding event. Potential benefits of this time-gated FRET approach include: eliminating background fluorescence, accessing two approximately independent FRET mechanisms in a single QD-bioconjugate, and multiplexed biosensing based on spectrotemporal resolution of QD-FRET without requiring multiple colors of QD.

The luminophores (FRET partners) used in this technique may be varied as desired. In addition to the commercially available Lumi4®-Tb (Lumiphore, Richmond, Calif., USA) used in the examples, other long lifetime FRET donors could be used including various luminescent lanthanide complexes (chelates or cryptates) based on $Tb^{3+}$, $Eu^{3+}$, $Sm^{3+}$, $Tm^{3+}$, and the like. Ruthenium complexes may also exhibit a sufficiently long excited state lifetime to serve as long lifetime FRET donors. Similarly, Cy5, Atto647, and many other fluorescent dyes or any other short-lifetime fluorophore (e.g. fluorescent proteins) may take the place of the Alexa Fluor 647 (Invitrogen by Life Technologies, Carlsbad, Calif., USA) employed in the examples. Different QD intermediates, including CdTe/ZnS and InP/ZnS QDs (etc.) can be used as well as the CdSe/ZnS QDs used in the examples (Invitrogen by Life Technologies).

Methodology

Reagents.

Figure 8:
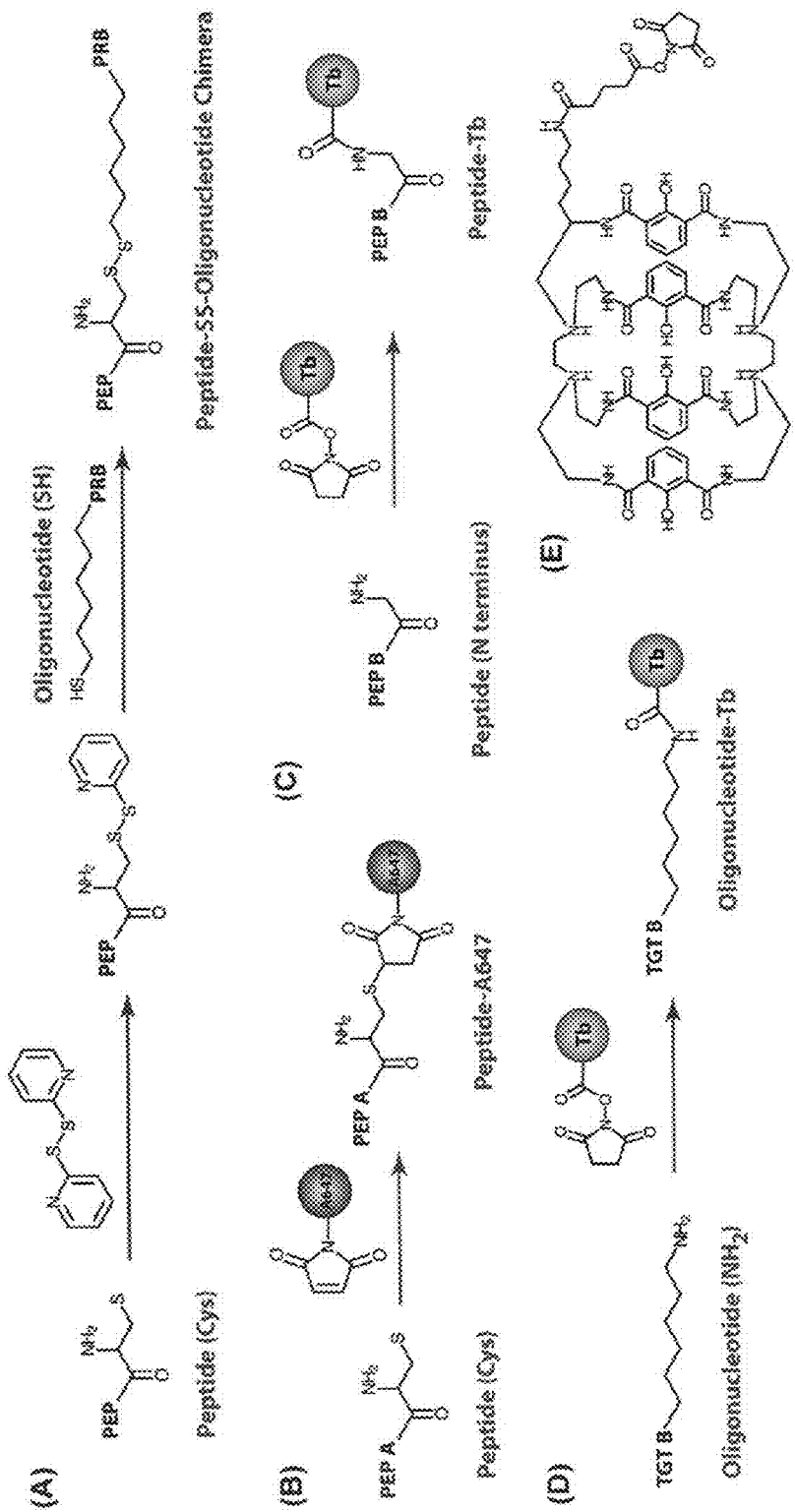
FIG. 8 illustrates exemplary bioconjugate chemistries. (A) Pyridyl disulfide activation of thiolated-peptide and a disulfide exchange reaction to prepare $His_6$-peptide-oligonucleotide chimeras. (B) A647-maleimide PEP A labeling at an N-terminal cysteine residue. (C) Tb-NHS PEB B labeling at the N-terminus. (D) Tb-NHS labeling at an amino modified linker of TGT B. Actual linker structures shown for the amine and thiol reactions. (E) Lumi4® NHS ligand structure ($Tb^{3+}$ omitted for clarity)

CdSe/ZnS QDs were obtained from Invitrogen by Life Technologies (Carlsbad, Calif.) and functionalized with dihydrolipoic acid-appended poly(ethylene glycol) (PEG, MW-750) ligands (see refs. 24 and 25). Peptides were synthesized as described in refs. 26 and 27 and labeled using A647 maleimide (Invitrogen) or Lumi4® $Tb^{3+}$ N-hydroxysuccinimide (NHS) complex (Tb; Lumiphore, Richmond, Calif.) (see ref. 28). Probe and complementary target oligonucleotides were obtained from Integrated DNA Technologies (Coralville, Iowa). Targets were labeled with A647 or Tb; probes were modified to hexahistidine ($His_6$)-DNA-peptide chimeras as described in ref. 27. Peptide and oligonucleotide sequences are given in Table 1, and the labeling chemistry is shown in FIG. 8

TABLE 1

Peptide and oligonucleotide sequences. Amino acid residues are capitalized in normal font; nucleotides are given in lower case italics.

Peptides (written N- to C-terminal):

PEP A[1]   (A647)-CSTRIDEANQRATKLP$_7$SH$_6$ (SEQ. ID No: 1)

PEP B[2]   (Lumi4™ $Tb^{3+}$)-GSGAAAGLSH$_6$ (SEQ. ID No: 2)

Oligonucleotides (PRB = probe, TGT = target):

PRB A[3]   3'-*tta gtt ctg tta taa caa*-5'-CGSGAAAGLSH$_6$ (SEQ. ID Nos: 3 and 4)

TGT A      5'-*aat caa gac aat att gtt*-3'-(A647) (SEQ. ID No: 5)

PRB B[3]   3'-*caa cat cct aat tga ctt*-5'-CGSGAAAGLSH$_6$ (SEQ. ID Nos: 6 and 4)

TGT B[2]   5'-*gtt gta gga tta act gaa*-3'-(Lumi4™ $Tb^{3+}$) (SEQ. ID No: 7)

[1]Peptide labeled at the cysteine (thiol).
[2]Peptide labeled at the N-terminus (1° amine), oligonucleotide labeled at a 3'-amino linker.
[3]Peptide-oligonucleotide chimeras are linked by a disulfide bridge between the peptide cysteine residue and 5'-thiol linker on the oligonucleotide.

Instrumentation and Photoluminescence (PL) Measurements.

PL spectra were acquired using a Tecan Infinite M1000 Dual Monochromator Multifunction Plate Reader equipped with a xenon flash lamp (Tecan, Research Triangle Park, N.C.). Non-gated PL emission spectra: 400 Hz flash frequency, 400 nm excitation, ~0 μs delay between flash and data acquisition, and a 40 μs integration time. Time-gated PL emission spectra: 100 Hz flash frequency, 339 nm excitation, 55 μs delay, 1 ms integration time. Tb/QD PL decay time measurements were acquired using three different systems (PLD systems 1-3), each with optimized capabilities for different decay.

PLD system 1 measurements were made using a customized spectrometer system with a 355 nm Nd:YAG laser source (60 Hz, 5 ns pulse width; 1 μJ per pulse) and monochromator for emission wavelength selection, analog PMT signals were processed using a digital oscilloscope and the time resolution was 40 μs, and a 55 μs time-gate was used.

PLD system 2 measurements were made using a modified KRYPTOR plate reader (Cezanne, Nimes, France) system with 4000 detection bins at 2 μs integration steps over 8 ms. A nitrogen laser was used for excitation (337.1 nm, 20 Hz, ~100 μJ per pulse). To detect Tb PL, a 494±20 nm bandpass filter was used; to detect Tb-sensitized QD PL, a 640±14 nm bandpass filter was used.

PLD system 3 measurements used a PicoQuant FT 300 fluorescence spectrometer, with samples at 40 nM concentration in borate buffer, pH 8.5, with a 1 MHz repetition rate and emission collected at 620±5 nm. The QD PL decay lifetimes were measured with excitation at both 330 nm and 405 nm (which are close to the wavelengths used for excitation in time-gated and non-gated PL spectrum measurements). The values reported are the intensity averaged PL lifetime from a triexponential fit.

QD Bioconjugates and Assays.

A647/Tb labeled peptides/oligonucleotides were conjugated to QDs via polyhistidine self-assembly by mixing at the desired stoichiometric ratios, in buffer, for 30-60 min. No purification was necessary, and the well characterized, high-affinity binding resulted in nearly quantitative assembly to the QDs (see refs. 22 and 29-31). Quantitation using the Tb/A647 absorption of the labeled peptides provided knowledge of the number of donors/acceptors per QD. For characterization experiments, the QD conjugate concentration was 45 nM (5 pmol). Time-gated proteolytic assays were done by preparing (PEP B-Tb)$_{10}$-QD-(PEP A-A647)$_3$ conjugates, adding trypsin, and tracking time-gated PL at 625 and 675 nm over 1.5 h at 2 min intervals. The final QD conjugate concentration was 0.2 μM (20 pmol). Time-gated hybridization assays were done by mixing TGT A-A647 (0-50 pmol) with 60 pmol of PRB A, hybridized 60 min, and (PEP B-Tb)$_{10}$-QD conjugates added, and time-gated PL spectrum measured after 60 min. The final QD conjugate concentration was 45 nM (5 pmol). Two-plex hybridization assays were done similarly, except that TGT A (0-50 pmol) and TGT B (0-80 pmol) were mixed with 50 pmol of PRB A and 80 pmol of PRB B prior to addition of unconjugated QDs. Both non-gated and time-gated PL spectra were measured.

Results

Peptides and peptide-oligonucleotide chimeras used were engineered to display terminal His$_6$ metal-affinity sequences to provide spontaneous self-assembly to the Zn$^{2+}$-rich QD surface. As noted in refs. 22, 29, and 30, this motif has been used to prepare QD bioconjugates of proteins, peptides, and oligonucleotides with excellent control over the conjugate valence. Characterization of His$_6$ self-assembly to QDs confirmed that an average of 50±10 peptides can be assembled around a ~6 nm diameter DHLA-capped QD. The 625 nm emitting QDs used here were coated with a similar ligand but were ~10±1 nm in diameter, suggesting access to an even wider range of conjugate valences. Since these experiments required the assembly of peptides and oligonucleotides, the latter were chemically ligated with a His$_6$-appended peptide as described in ref. 29 (FIG. 8 and Table 1) to ensure a level of control that was analogous to peptide assembly. In turn, labeling the peptides or oligonucleotides with Tb and/or A647 (FIG. 8) enabled excellent control over the number of Tb and A647 assembled per QD; this permitted characterization of the FRET$_1$ and FRET$_2$ processes (depicted in FIG. 1A) during stepwise changes in donor-acceptor stoichiometry. The schematic constructs in FIG. 1B summarize the three different QD bioconjugates used here: (i) peptides, (ii) peptide-oligonucleotide chimeras, and (iii) hybrid assemblies of peptides and peptide-oligonucleotide chimeras. Since assembly of these labeled materials to the QD yields an approximately centrosymmetric FRET configuration, it was possible to treat all of the Tb or A647 in a given assembly as being equivalent within the Förster formalism.

Donor-Acceptor Pairs and Spectral Overlap.

Figure 2:
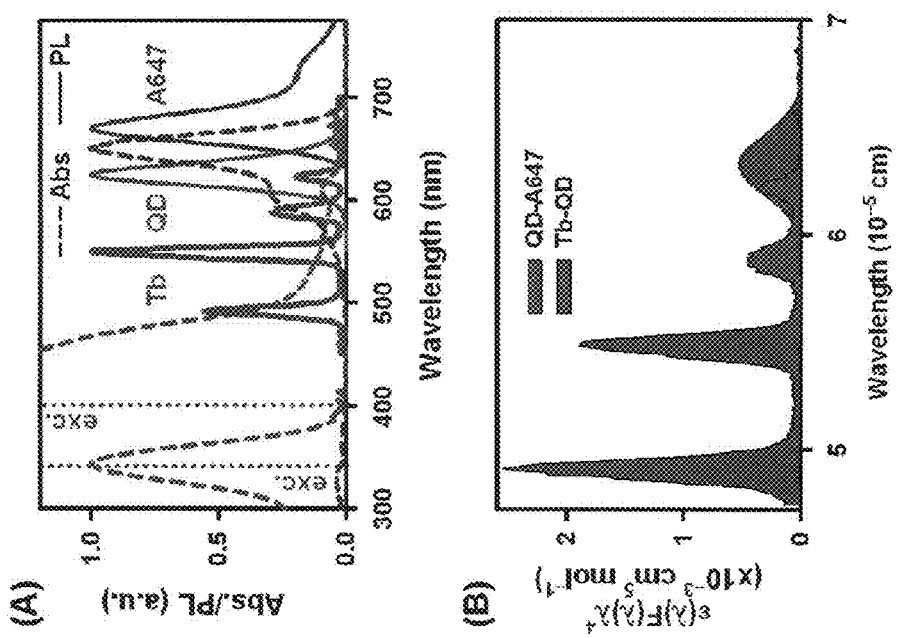
FIG. 2A shows absorbance and PL spectra for the $Tb^{3+}$ complex (with a peptide in a complex termed PEP B-Tb) (the compositions of this and other complexes are detailed below), red-emitting CdSe/ZnS core/shell QDs, and A647 dye (as PEP A-A647); 339 and 400 nm excitation are shown for reference.
FIG. 2B shows spectral overlap functions for the Tb-QD and QD-A647 FRET pairs.

Red-emitting 625 nm PL QDs (27 nm full-width-at-half-maximum) were paired as both an acceptor for the initial Tb donor, and a subsequent donor for the A647 acceptor. FIG. 2 shows the absorption and PL spectra for the Tb, QD and A647, as well as the spectral overlap functions for the Tb-QD and QD-A647 FRET pairs. FIG. 2A shows absorbance and PL spectra for the Tb$^{3+}$ complex (as PEP B-Tb), red-emitting CdSe/ZnS QDs, and A647 dye (as PEP A-A647); 339 and 400 nm excitation are shown for reference. FIG. 2B shows spectral overlap functions for the Tb-QD and QD-A647 FRET pairs. Photophysical and FRET parameters for the different luminophores and donor-acceptor combinations are listed in Table 2. The Tb$^{3+}$ complex incorporates a proprietary isophthalamide-type ligand that sensitizes the lanthanide ion, which otherwise has a prohibitively low direct molar absorptivity, as noted in refs. 28 and 33. The Tb was optimally excited at 339 nm and exhibited sharp emission lines at ~490, 550, 585 and 620 nm. The QD was efficiently excited at 339 nm ($\epsilon_{QD} \approx 1.9 \times 10^7$ M$^{-1}$ cm$^{-1}$) and 400 nm ($\epsilon_{QD} \approx 1.1 \times 10^7$ M$^{-1}$ cm$^{-1}$). In contrast, the A647 was only very weakly excited at these wavelengths ($\epsilon_{A647} \leq 1 \times 10^4$ M$^{-1}$ cm$^{-1}$).

TABLE 2

Optical characteristics of Tb, QD and A647 luminophores with their FRET pairs.

| Luminophore | $\epsilon_{max}$ (M$^{-1}$ cm$^{-1}$)[$\lambda_{max}$] | $\epsilon$(M$^{-1}$ cm$^{-1}$)[$\lambda_D$]$^a$ | Φ | τ |
|---|---|---|---|---|
| Tb | 26 000 [339 nm] (Lumi4 ligand) | — | 0.77 ± 0.10 (Tb$^{3+}$) | 2.6 ± 0.2 ms |
| QD | 5.5 × 10$^5$ [610$^b$ nm] | 5-50 × 10$^5$ [475-575 nm] | 0.55 ± 10 | 50 ± 3 ns |
| A647 | 239 000 [650 nm] | 89 000 [625 nm] | 0.33$^c$ | ~1 ns$^d$ |

| FRET pair (D → A)$^e$ | J (mol$^{-1}$ cm$^6$) | R$_0$ (nm) |
|---|---|---|
| Tb → QD | 7.2 × 10$^{-9}$ | 10.1 |
| QD → A647 | 1.8 × 10$^{-9}$ | 7.5 |

| FRET pairs (D → A)$^e$ | r$_{pred.}$ (nm)$^f$ | r$_{meas.}$ (nm) | FRET modality |
|---|---|---|---|
| PEPB-Tb → QD$^g$ | 6.2-6.7 | 6.3 | FRET$_1$ (Tb lifetime quenching) |
| QD → PEPA-A647$^h$ | 7.7-8.2 | 8.4 | FRET$_2$ (QD PL quenching) |
| QD → PEPA-A647$^i$ non-gated with (PEPB-Tb)$_{10}$ | 7.7-8.2 | 8.3 | FRET$_2$ (QD PL quenching) |

TABLE 2-continued

Optical characteristics of Tb, QD and A647 luminophores with their FRET pairs.

| QD → PEPA-A647[j] time-gated with (PEPB-Tb)[10] | 7.7-8.2 | 8.1 | FRET$_2$ (QD PL quenching) |
|---|---|---|---|

[a]Extinction coefficient at peak donor PL emission wavelength, $\lambda_D$.
[b]Extinction coefficient at first exciton peak.
[c]Source: Invitrogen by Life Technologies.
[d]Source: ref.[55]
[e]Written as donor to acceptor.
[f]Geometric prediction based on QD and peptide dimensions.
[g]Tb → QD measured from Tb PL decay quenching.
[h]QD → A647 measured from QD PL quenching following direct QD excitation.
[i]QD → A647 measured from non-gated QD PL quenching following direct QD excitation (PEP B-Tb also present on QD).
[j]QD → A647 measured from time-gated QD PL quenching following FRET$_1$ sensitization.

The large Förster distance calculated for Tb-to-QD energy transfer (10.1 nm) was a product of the extremely strong absorption of the QD across the emission range of the first three Tb lines. The Förster distance of the QD-A647 FRET pair was 7.5 nm, and this value is among the largest noted when pairing a QD donor with a dye acceptor (typically, $R_0 < 6$ nm). Examining the Tb-QD-A647 three-luminophore system a priori confirmed the potential for a multistep FRET$_1$ + FRET$_2$ relay process wherein excited-state Tb can transfer energy to the QD (acceptor), which subsequently acts as a donor for the A647, resulting in a net energy transfer from the Tb to the A647. The putative Tb-A647 FRET pair had significant spectral overlap and a Förster distance of 5.7 nm ($J = 2.5 \times 10^{-10}$ mol$^{-1}$ cm$^6$); however, the FRET$_1$ and FRET$_2$ pathways should be more favored since, based on the relative Förster distances, their rates are expected to be 30-fold and 5-fold faster than Tb-to-A647 energy transfer, respectively.

Intensity-Based Analysis of Tb-to-QD Energy Transfer (FRET$_1$).

Initial experiments focused on determining the degree to which the Tb could sensitize time-gated QD PL via FRET$_1$. Increasing ratios of Tb-labeled PEP B (PEP B-Tb) were assembled on the 625 nm QDs and the resulting PL spectra were collected in both non-gated (~0 μs delay) and time-gated modes (see Materials and Methods section for exact definitions). Time-gating for the measurements was empirically selected to be 55 μs, which corresponded to the minimum delay after flash excitation needed to minimize signal from direct excitation of the QDs. The residual signal was due to an instrumental/electronic echo effect rather than residual PL, as the QD excited-state completely decayed in less than a microsecond. An integration time of 1 ms was selected for time-gated measurements to be commensurate with the typical excited-state lifetimes of Tb complexes (see ref. 33). Without time-gating, the Tb sensitization of QD PL could not be observed over the directly excited QD PL.

As shown in FIG. 3A, an approximately linear increase in the time-gated, Tb-sensitized QD PL was observed as the valence of PEP B-Tb assembled per QD was incrementally increased from 0 to 20 Tb per QD. An analogous experiment using the same ratios of prehybridized Tb-labeled TGT B/PRB B peptide-DNA chimeras (PRB B/TGT B-Tb) is shown in FIG. 3B, and also revealed an approximately linear increase in QD sensitization. Increased time-gated QD sensitization was also observed beyond 20 Tb per QD, but the linear trend was not always consistent. In the case of the PRB B/TGT B-Tb loading, non-specific QD adsorption of TGT was found to be negligible. The long excited-state lifetime of the Tb provided sufficient time for the QD to relax to its ground state (following flash excitation) and function as an effective FRET acceptor. In turn, the time-gating provided a mechanism to monitor this process. The time-gated QD PL signal was minimal in the absence of assembled Tb, confirming that the His$_6$-mediated selective attachment of the Tb-labeled peptides/oligonucleotides to the QD, and thereby sensitized the time-gated QD PL.

The Tb functioned as an effective FRET donor for the QD irrespective of whether it was directly labeled onto a peptide terminus (PEP B-Tb) or indirectly through oligonucleotide hybridization (PRB B/TGT B-Tb). The slightly lower rate of QD sensitization or FRET efficiency for the latter is believed to arise from a slightly longer Tb-QD separation in the DNA incorporating configuration. The Tb was attached at the end of a six-carbon aminated linker, which can allow some freedom of movement, in addition to breathing of the oligonucleotide hybrids. Moreover, previous results suggest that dye labels assembled onto QDs using similar peptide-DNA chimeras can have a wide range of movement relative to the QD (see ref. 34). Regardless, assembling greater numbers of Tb around the central QD increased the rate of energy transfer from Tb donors to QD acceptors, and this effect was observed as increases in the time-gated QD PL sensitization.

To further assess FRET$_1$, the excitation spectra of (PEP B-Tb)$_{10}$-QD conjugates were measured with and without time-gating, as shown in FIG. 3C. In both cases, the Tb emission (monitored at 490 nm), gave rise to the characteristic PEP B-Tb excitation/absorption peak centered at 339 nm. In contrast, monitoring the QD PL (at 625 nm) produced three very different results. The characteristically broad QD excitation/absorption spectrum was observed without time-gating for QD alone or (PEP B-Tb)$_{10}$-QD conjugates. With time-gating, the QD alone yielded no signal, whereas (PEP B-Tb)$_{10}$-QD conjugates exhibited the characteristic Tb excitation/absorption peak centered at 339 nm. The latter indicated that energy absorbed by the Tb was being reemitted by the QD. These results provided additional confirmation of QD sensitization by the Tb once the QD had returned to its ground state following direct optical excitation. It should be noted that marked quenching of the Tb donor PL intensity—especially at higher assembly ratios—could not be consistently observed in the time-gated PL spectra. This result did not allow for measurement of FRET efficiency directly from the donor PL loss and is in contrast to previous formats where QD donors were assembled with an increasing number of acceptors, resulting in progressive quenching of the QD PL (see refs. 20 and 35-38). However, given the multiple donor-single acceptor configuration, this behavior was not unexpected.

PL Decay Analysis of Tb-to-QD Energy Transfer (FRET$_1$).

Figure 4:
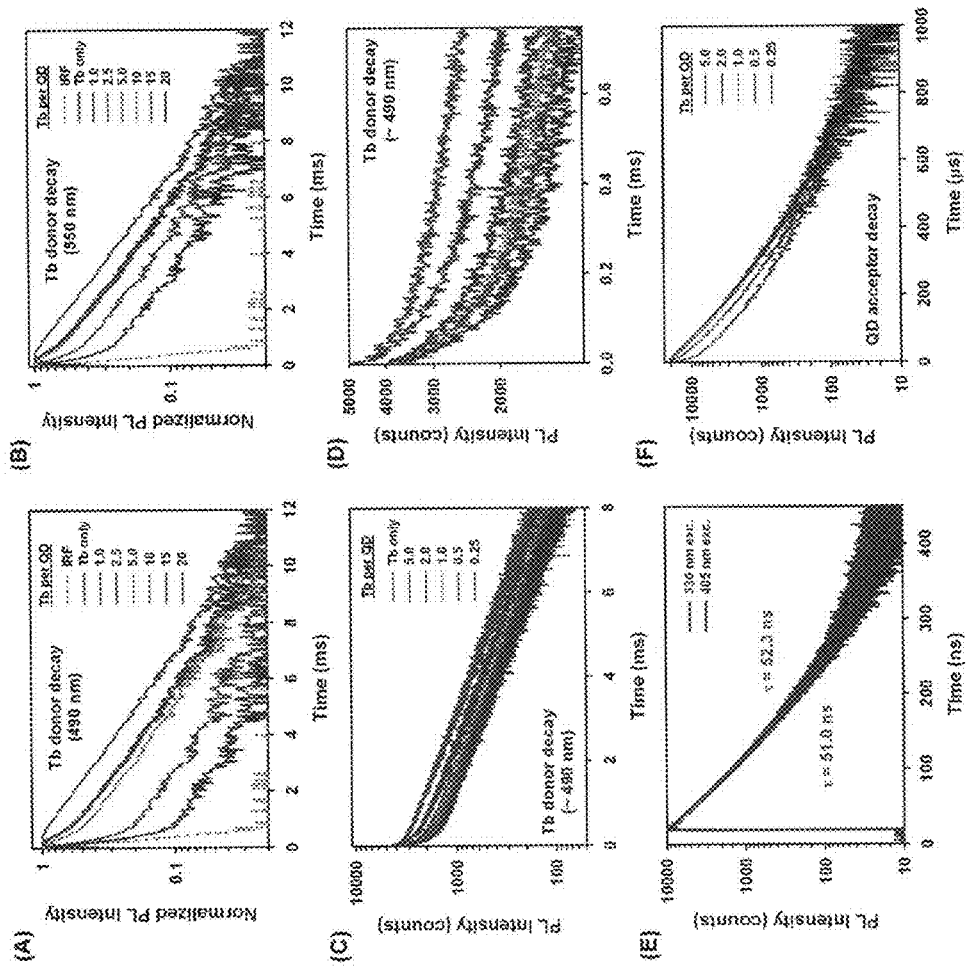
FIG. 4 shows Tb donor PL decay curves collected at (A) 490 nm and (B) 550 nm for different PEP B-Tb per QD ratios. (C) Higher-resolution donor PL decay curves collected at 490 nm for the indicated PEP B-Tb per QD ratios. (D) Magnified view of the short PL lifetime component for the data in (C). The small fraction of short PL lifetime component in the green (Tb only) curve is an artifact or echo from the detection setup. (E) Native QD PL decay curves. (F) $FRET_1$-sensitized QD PL decay curves at different PEP B-Tb per QD ratios. The QD reflects the ~$10^2$ μs lifetime associated with energy transfer from the Tb.

Further characterization and confirmation of Tb-to-QD energy transfer was obtained using PL decay time analyses. Measurements of the Tb PL lifetimes were first collected, using PLD system 1, as the number of PEP B-Tb assembled per QD was increased. As shown in FIGS. 4A-B, the Tb lifetimes were monitored at both the 490 and 550 nm emission lines. In the absence of QD, the PEP B-Tb had a monoexponential PL decay with a characteristic lifetime of ca. 2.6-2.7 ms. When an average of ~1 PEP B-Tb was assembled per QD, the PL decay became distinctly multiexponential, showing a fast decay component and a residual long-lifetime component that paralleled the native Tb lifetime. As the average number of PEP B-Tb was increased to 2.5, 5, 10, 15 and 20 per QD, the relative contribution of the native, long-lifetime component increased significantly; however, the fast decay component did not fully disappear. At >10 PEP B-Tb per QD, the ratio of the fast and native decay components saturated to a constant value. This behavior was reflected in both the 490 and 550 nm Tb PL lines, although for the 550 nm line, the fast decay appeared more attenuated compared to the native, long-lifetime component of the Tb. This disparity coincided with the relative brightness of the Tb lines (550 nm>490 nm; see FIG. 2A.

The appearance of the very fast decay component was consistent with very efficient energy transfer from the Tb to QD, as expected based on the large $R_0$ of 10.1 nm for this FRET pair. It was estimated that the PEP B-Tb places the Tb≦1.2 nm from the QD surface and ~6.7 nm from the QD center. This value was arrived at by considering: (1) a negligible contribution from the $His_6$-terminus which is in direct contact with the ZnS shell, (2) the $Ala_3$ tract forming a helix that is disrupted by the flanking glycine residues, (3) rotational flexibility in the peptide, and (4) comparison to donor-acceptor distances for similarly sized peptides determined previously (see ref. 38). The QD radius was estimated to be 5.5 nm. As the Tb donor-QD acceptor separation (r≈6.7 nm) was much shorter than the Förster distance (10.1 nm), a FRET efficiency exceeding 92% was expected. The short Tb lifetime component was between ca. 20-200 μs and suggested $FRET_1$ efficiencies of 93-99%. However, these short lifetimes were comparable to the temporal resolution (40 μs) of PLD system 1 measurements; further experiments were done at higher resolution (2 μs bins) using PLD system 2. Representative data measured for different ratios of Tb per QD (490 nm emission line) are shown in FIGS. 4C-D and summarized in Table 3. The short, QD-quenched, Tb decay component(s) were analyzed and yielded an average lifetime of 150±60 μs, which corresponded to a $FRET_1$ efficiency of approximately 94±3%. Based on this data, the rate of $FRET_1$ is estimated to be $6.3 \times 10^3$ s$^{-1}$.

TABLE 3

$FRET_1$ efficiencies determined from $FRET_1$-quenched Tb PL decay lifetimes and $FRET_1$-sensitized time-gated QD PL decay lifetimes (collected with PLD system 2).

| | Tb PL (490 nm) | | | QD PL | |
|---|---|---|---|---|---|
| Tb per QD | Tb-FRET $\tau_{av}$ (μs) | $\tau_3 = \tau_{Tb}$ (ms) | $E_{Tb}{}^a$ | QD-FRET$\tau_{av}$ (μs) | $E_{QD}{}^b$ |
| 0 | — | 2.72 | — | 0.05$^c$ | 0 |
| 0.5 | 159 | 2.72 | 0.95 | 133 | 0.95 |
| 1 | 172 | 2.73 | 0.95 | 119 | 0.96 |
| 2 | 136 | 2.74 | 0.94 | 114 | 0.96 |
| 5 | 126 | 2.72 | 0.94 | 113 | 0.96 |

$^a$$FRET_1$ efficiency from fast Tb PL decay component.
$^b$$FRET_1$ efficiency from time-gated sensitized QD PL decay.
$^c$QD in the absence of FRET; measured with PLD system 3 (see Supporting Information).

Due to electronic saturation of PLD system 2 at short time-scales, some residual fast decay component appeared in the PEP B-Tb decay curves (see FIG. 4D). This was a result of the high sensitivity of PLD system 2 and its optimization for long-lifetime measurements. Although this contribution was very small, it was important to compare the lifetime results from the Tb donor decays with the Tb-sensitized QD PL decays. The latter are proof of FRET since microsecond to millisecond QD PL decay can only result from FRET-sensitization. The QDs had a native PL lifetime of ca. 50 ns following direct optical excitation (see FIG. 4E), however, with assembly of PEB B-Tb, the QD manifested a 120±30 μs PL lifetime that was significantly increased (2400-fold) and commensurate with the fast Tb PL decay component. FIG. 4F shows plots of the Tb-sensitized, QD acceptor PL decays at the same ratios of PEP B-Tb used in FIGS. 4C-4D. This result was conclusive evidence of the $FRET_1$ pathway and corresponded to an efficiency of 95±3%, which was in good agreement with that estimated from the Tb PL decay. Assuming a $FRET_1$ efficiency between 91-98%, the Tb-QD center-to-center separation distance in (PEP B-Tb)$_n$-QD conjugates was calculated to be between 5.3-6.9 nm (6.3 nm for the median 94.5% efficiency). This value was also in good agreement with the estimated length of PEP B plus the QD radius (~6.7 nm), despite the intrinsic insensitivity of FRET to changes in donor-acceptor separation distance at very high efficiencies.

QD-to-A647 Energy Transfer ($FRET_2$).

Figure 5:
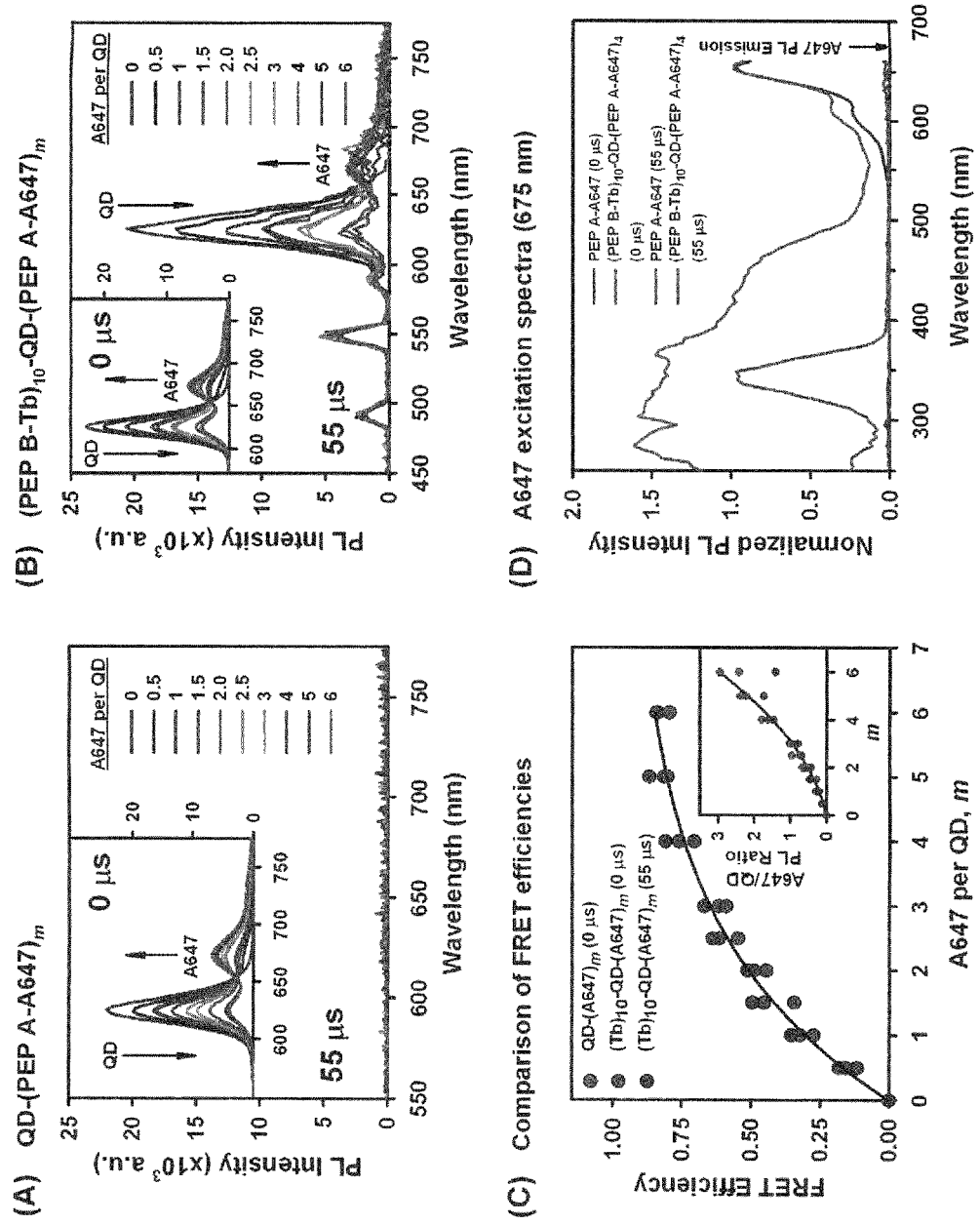
FIG. 5A shows non-gated (~0 μs) and time-gated (55 μs) PL spectra for QD-(PEP A-A647), assemblies with increasing A647 ratio or valence (m). No PL was observed in the time-gated spectrum.
FIG. 5B shows PL spectra of (PEP B-Tb)$_{10}$-QD-(PEP A-A647)$_m$ assemblies. QD and A647 PL are apparent in both the non-gated and time-gated spectra.
FIG. 5C shows correlation of the FRET efficiencies as a function of A647 valence between the three different sets of PL spectra in (A) and (B), calculated from the degree of QD donor quenching. The inset shows the corresponding A647/QD PL ratios.
FIG. 5D shows A647 PL excitation spectra for the different configurations, illustrating both $FRET_1$ and $FRET_2$ sensitization.

The second QD-to-A647 energy transfer ($FRET_2$) step in the FRET relay was examined. Increasing ratios of A647-labeled PEP A (PEP A-A647) were self-assembled around the central QD, and the non-gated and time-gated PL emission spectra measured. As shown in FIG. 5A, increasing the ratio of PEP A-A647 assembled per QD resulted in the progressive quenching of QD PL and sensitization of A647 PL via $FRET_2$ in the non-gated PL spectrum. Analogous measurements of equivalent amounts of PEP A-A647 without QD revealed negligible directly excited acceptor emission, confirming efficient FRET and significant reemission by the acceptor. The observed trends of increasing donor/acceptor quenching/ sensitization were analogous to those observed with other QD donor-multiple dye acceptor FRET pairs (see refs. 20 and 35-38). The time-gated PL spectrum of these conjugates revealed only background noise and no traces of QD or A647 PL. Fitting the non-gated FRET data with the Förster model yielded an average donor-acceptor separation of r≈8.4 nm for the QD-(PEP A-A647)$_m$ conjugates. This value agreed with predictions. In addition to a QD radius of ~5.5 nm, PEP A comprised a $Pro_7$ motif that forms a type-II helix ~1.2 nm in length (see ref. 39) and 15 additional residues that contribute 1-1.5 nm of length. The overall separation was thus r≈7.7-8.2 nm. The maleimido linker in the dye structure will also contribute some extra length. Based on an average r≈8.3 nm (vide infra) and an intrinsic QD lifetime of 50 ns, the rate of $FRET_2$ was estimated at $1.1 \times 10^7$ s$^{-1}$ per acceptor. This rate corresponds to ca. 36% FRET efficiency for the first A647 acceptor.

Tb-to-QD-to-A647 Time-Gated FRET Relay ($FRET_1$+$FRET_2$).

For the next FRET characterization, PEP B-Tb and PEP A-A647 were co-assembled around the central QD to yield the final Tb-to-QD-to-A647 energy transfer relay. Time-gated PL measurements were again critical for observing Tb-sensitization of the QD during $FRET_1$, and the subsequent energy transfer from the QD to the A647 in $FRET_2$. To allow simple resolution of the effect of $FRET_1$ on $FRET_2$, the PEP B-Tb ratio was fixed at an intermediate value of 10 per QD. This valence corresponded to a significant rate of QD sensitization (see FIG. 3) while still leaving a large amount of the QD surface available for assembling PEP A-A647, which was added at ratios between 0-6 per QD. As shown in the inset of FIG. 5B, the non-gated PL emission spectrum of the full conjugate revealed the QD PL quenching and sensitization of A647 PL characteristic of directly excited $FRET_2$ and similar to that of QD with only A647 shown in FIG. 5A. It can be seen that the data in the FIGS. 5A and 5B insets are nearly superimposable and analysis yielded an estimated QD-A647 separation of r≈8.3 nm in the (PEP B-Tb)$_{10}$-QD-(PEP A-A647)$_m$ conjugates without time gating—a value that deviated less than 2% from that measured for the non-gated QD-(PEP A-A647)$_m$ conjugates (see Table 2). Coassembly of ~10 PEP B-Tb on the central QD thus had little effect on the directly excited $FRET_2$ pathway.

FIG. 5B shows the time-gated PL emission spectra of the (PEP B-Tb)$_{10}$-QD-(PEP A-A647)$_m$ conjugates. In addition to Tb PL, both QD and A647 PL were observed. Even with sensitization from the $FRET_1$ pathway rather than direct optical excitation, the QD PL showed the same progressive quenching with an increasing ratio of PEP A-A647 acceptor per QD. Similarly, the A647 showed a corresponding pattern of $FRET_2$-sensitized PL that increased with its valence. Notably, the Tb PL was not significantly quenched by the addition of PEP A-A647, underlining the approximate independence of $FRET_1$ and $FRET_2$. Analysis of the time-gated QD PL quenching derived an average QD-A647 separation of r≈8.1 nm—a less than 3% deviation from the other two data sets (see Table 2). These two results confirmed that the intrinsic properties of $FRET_2$ were carried over into the time-gated measurements sensitized by $FRET_1$. All three data sets are quantitatively compared in FIG. 5C; they match extremely well and can all be fit to the Förster formalism. The average QD-A647 separation across the three data sets was r≈8.3 nm. Moreover, separate analysis of the FRET efficiency at each A647 valence across all three QD-to-A647 data sets yielded, on average, a relative standard deviation <10%. In addition, the A647/QD acceptor/donor PL ratio was also determined and compared between the same data sets. A good correspondence is seen across the different PEP A-A647 valences, except for small negative deviations in the time-gated data at 5-6 PEP A-A647 per QD. The latter is believed to arise from poorer instrumental signal-to-noise (S/N) at the A647 wavelengths within the time-gated measurement settings, rather than a modification of $FRET_2$ (similarly, S/N is poorer for Tb in non-gated measurements). This data also suggested that there was no significant "extra" sensitization of the A647 via direct Tb-to-A647 FRET, in agreement with our a priori expectations based on relative energy transfer rates.

To further establish the $FRET_1$+$FRET_2$ relay, excitation spectra were collected with PEP A-A647 and (PEP B-Tb)$_{10}$-QD-(PEP A-A647)$_4$ conjugates, as shown in FIG. 5D. The PEP A-A647 valence was fixed at 4 per QD to ensure efficient but non-saturated FRET. The excitation spectra were collected at 675 nm, corresponding to A647 PL emission. PEP A-A647 alone was characterized by its own excitation/absorption profile without time-gating and gave rise to no measureable excitation spectrum with time-gating. In contrast, the (PEP B-Tb)$_{10}$-QD-(PEP A-A647)$_4$ conjugate excitation spectrum was a composite of the A647 and QD excitation/absorption profiles without time-gating. This was indicative of direct excitation and $FRET_2$, respectively. Importantly, with time-gating, the excitation spectra corresponded to that of the Tb, unequivocally demonstrating that the time-gated sensitization of the A647 originated from the Tb via consecutive $FRET_1$ and $FRET_2$ processes at the QD. Cumulatively, the data collected to this point also suggested that $FRET_1$ and $FRET_2$ were approximately independent of one another (time-gated sensitization notwithstanding).

Proteolytic Assays.

Protease sensing using the FRET relay assembly was investigated in a time-gated, kinetic mode to examine possibilities of this technique in biosensing. This utilized PEP A-A647 and PEP B-Tb along with trypsin—a prototypical serine protease that cleaves on the C-terminal side of arginine and lysine residues. To enable sensing, PEP A incorporated one lysine (K) and two arginine (R) cleavage sites along its length (see ref. 40). In contrast, PEP B contained no lysine or arginine residues, and was therefore not a potential substrate for trypsin (confirmed experimentally; data not shown). The time-gated QD-FRET relay monitored trypsin activity by following the loss of $FRET_2$ from proteolysis of PEP A-A647. Analogous to previous QD-FRET configurations for sensing proteolytic activity (see refs. 36, 38, and 40) the initial state of this time-gated configuration was "ON" with respect to the QD-A647 $FRET_2$ pair, as illustrated in FIG. 1B(i). Proteolysis decreased the number of A647 proximal to the QD, progressively shifting the system toward a $FRET_2$ "OFF" state with increasing activity, and thus provided a dynamic signal. In parallel, PEP B-Tb provided approximately constant time-gated sensitization of the QD by $FRET_1$. (PEP B-Tb)$_{10}$-QD-(PEP A-A647)$_3$ conjugates were selected since 10 equivalents of PEP B-Tb provided significant time-gated QD sensitization, and 3 initial equivalents of PEP A-A647 afforded maximal changes in FRET efficiency during subsequent proteolysis. In contrast to previous configurations, time-gated sensing could be accomplished due to the $FRET_1$ pathway. Another novel feature was the measurement of protease activity in a kinetic mode, where the course of proteolysis was followed in real-time using two-color ratiometric measurements.

Figure 6:
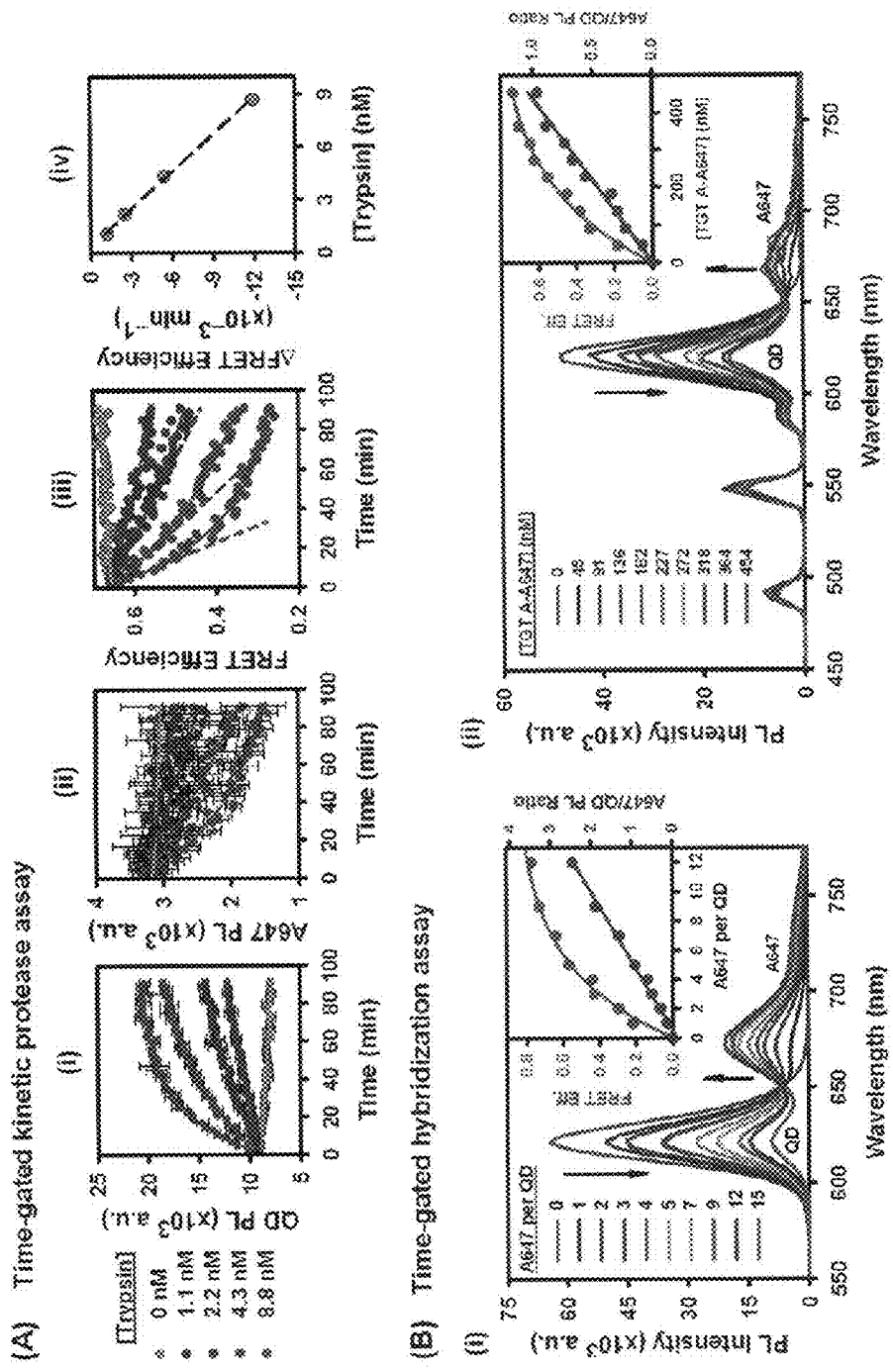
FIG. 6 shows time-gated biosensing configurations with a two-step QD-FRET relay.

As shown in FIG. 6A, exposing the FRET-relay protease sensor to increasing amounts of trypsin increased the rate at which FRET-sensitized QD PL recovered, and the rate at which $FRET_2$-sensitized A647 PL was lost. Accordingly, the time-dependent $FRET_2$ efficiency showed a commensurate decrease with the progression of proteolysis. The initial rate of change in the $FRET_2$ efficiency also increased linearly with increases in protease concentration. Control experiments with no trypsin showed consistent QD PL, A647 PL, and FRET efficiency over all time courses. For the unoptimized combination of QD-peptide substrate concentrations, trypsin preparation, sample conditions, and analysis time utilized herein, a limit of detection (LOD) was estimated to be 200 μM (0.5 ng) trypsin (using a threshold value of three standard-errors beyond the slope of the line of best fit through the FRET efficiency time course for the negative control at 0 nM trypsin). This LOD represents an approximately 3-fold and 30-fold improvement compared to the 625 μM or 6.25 nM previously estimated for a similar QD-FRET sensor assembled using the same peptide substrate (with smaller QDs and a different acceptor dye), but measured in a non-kinetic mode on a fluorescent plate reader or a custom microchip platform, respectively (see refs. 40 and 41). The improvement in LOD was surprising, given that the previous studies used QD-FRET sensors based on a single QD-to-dye FRET pathway. However, in this FRET relay, the efficiency of $FRET_1$ was very high (~94%) which minimized the loss of final acceptor sensitization due to the added energy transfer step. The increase in sensitivity can be attributed at least in part to the added kinetic analysis, which allows greater resolution of low activity proteolysis.

Time-Gated DNA Hybridization Assay.

A second sensing configuration explored using the FRET relay was a time-gated hybridization assay. To this end, QDs coassembled with PEP B-Tb and PRB A were employed.

Initial measurements were made without time-gating by mixing QDs with 15 equivalents of PRB A that had been prehybridized with increasing amounts of TGT A-A647, as a QD-(PRB A)$_{15}$/(TGT A-A647), configuration. As shown in FIG. 6B(i), the result was the expected rise approaching maximum FRET efficiency, and an approximately linear increase in the FRET-sensitized A647/QD PL ratio. The latter provided a more convenient (linear and no reference state needed) and sensitive capacity for quantitative detection. For the time-gated hybridization assay, (PEP B-Tb)$_{10}$-QD conjugates were co-assembled with 12 equivalents of PRB A to detect an increasing quantity of TGT A-A647, as shown in FIG. 1B(iii). Analogous to the time-gated protease construct, the role of PEP B-Tb was to provide time-gated sensitization of the QD PL in the final (PEP B-Tb)$_{10}$-QD-(PRB A)$_{12}$/(TGT A-A647), configuration. The latter time-gated PL spectrum revealed the expected FRET "ON" progression as the amount of hybridized TGT A-A647 increased, indicated by decreases in QD PL and corresponding increases in sensitized A647 PL. Between the non-gated and time-gated formats, the FRET$_2$ efficiency as a function of the number of equivalents of PEP A-A647 did not change (see FIG. 6B); however, the slope of the A647/QD PL ratio diminished, attributable to lower signal-to-noise for the A647 PL within the time-gated measurements. Quantitative time-gated data (FIG. 6B(ii)) was obtained from the linear increase in A647/QD PL ratio, and the LOD was estimated to be 16 nM (1.8 pmol). The LOD threshold, determined at ca. 670 nm, was set as three standard deviations above the average baseline QD PL spectrum in the region 660-775 nm. That is, the minimum amount of TGT A-A647 needed to have a reliably measureable A647 PL signal above the noise expected due to the QD crosstalk at ca. 670 nm, and with which to calculate an A647/QD PL ratio. A continuation of the linear trend in A647/QD PL ratio was noted at a 25% excess of TGT A-A647 over PRB A, suggesting that probe-target hybridization was less than 1:1. In terms of concentration, the 16 nM LOD was approximately an order of magnitude higher than the ~1 nM LODs previously reported for ensemble solution-phase and solid-phase hybridization assays (see refs. 42 and 43, respectively) based on QD-dye FRET pairs (no relay). Those assays used 500 and 1250 μL sample volumes (cf. 100 μL used herein), such that the LOD in terms of the absolute quantity of material was comparable (~0.5-1.3 pmol). However, as a ratiometric measurement, it should be noted that this value is a function of both the QD-bioconjugate concentration and sensitivity of the instrumentation. In our experiments, the limitation appeared to be the microplate reader, which was primarily designed for high-throughput analysis instead of high sensitivity spectrofluorimetry, and prevented the use of lower quantities of QD to detect smaller amounts of target. Nevertheless, these results confirmed that DNA hybridization could also be monitored using time-gated Tb-to-QD-to-A647 FRET.

Orthogonal Two-Plex DNA Hybridization Assay.

Another sensing configuration focused on exploiting the approximately independent FRET$_1$-FRET$_2$ mechanisms for signal transduction in a multiplexed format. It is apparent that the two different energy pathways could be increasingly sensitized by the assembly of more Tb or A647 per QD. In contrast to previous QD-based biosensing formats (see, e.g., ref. 44), the technique described herein provides a route to multiplexed detection that does not derive its information from the use of multiple QD colors, but rather from the temporal resolution of the FRET$_1$ and FRET$_2$ processes. It was desired to demonstrate that each FRET process could reflect a distinct biorecognition event and provide an orthogonal analytical signal.

Figure 3:
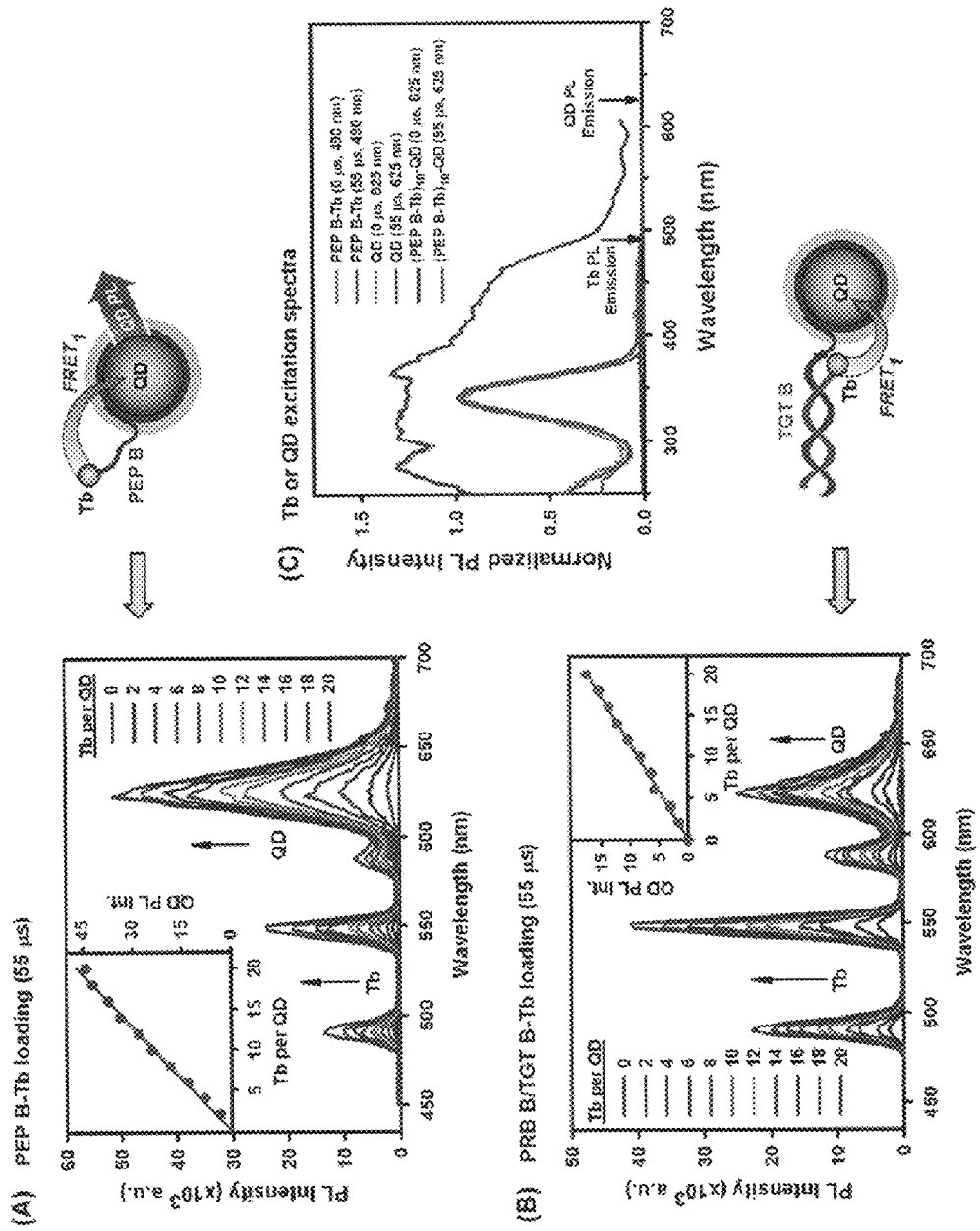
FIG. 3 shows time-gated (with a 55 μs delay before data collection) PL spectra showing the increasing $FRET_1$-sensitization of QD PL with an increasing amount of: PEP B-Tb (FIG. 3A) and PRB B/TGT B-Tb (FIG. 3B) (where "PRB" refers to a probe) hybrids (the valence of PRB B is consistently 20). In each case, the insets show an approximately linear increase in $FRET_1$-sensitized QD PL.

The magnitude of FRET$_1$-sensitized time-gated QD PL is linearly proportional to the amount of proximal Tb (see FIG. 3). Likewise, the A647/QD PL ratio can be linearly proportional to the amount of proximal A647 (see FIG. 5B). For a two-plex assay, the non-gated A647/QD PL ratio would reflect FRET$_2$ uniquely since the Tb signal is excluded from these measurements. Thus, any biomolecular binding event associating A647 with the QD could be detected orthogonally to any events associating the Tb with QD. The time-gated QD PL sensitization could be used to measure the extent of FRET$_1$ if the quenching effect of proximal A647 is accounted for. Thus, the total time-gated QD+A647 PL sensitization was used as an analytical signal for the extent of the FRET$_1$ process. A correction based on the A647 quantum yield was introduced to account for energy that was transferred from the QD, but not reemitted by A647. This analysis provided a working model and two predicted orthogonal analytical signals to verify experimentally. A DNA hybridization assay was selected since Watson-Crick base-pairing is a selective biorecognition event that can be readily designed to avoid cross-reactivity.

In conjunction with non-gated and time-gated measurements, a two-plex configuration was created by assembling (PRB B)$_{16}$-QD-(PRB A)$_{10}$ conjugates to respond to TGT B-Tb and TGT A-A647. The oligonucleotides were prehybridized with target, the QDs added, and self-assembly allowed to occur yielding (TGT B-Tb)$_n$/(PRB B)$_{16}$-QD-(PRB A)$_{10}$/(TGT A-A647)$_m$ conjugates for detection. FIG. 1B(ii) illustrates the generic bioconjugate structure, while the schematics in FIG. 7A depict the different permutations of target hybridization-mediated FRET within the bioconjugates at the four extremes of the assay: m=n=0; m=10, n=0; m=0, n=16; and m=10, n=16. The first permutation (i) corresponded to an absence of target and only the QD, which gave rise to QD PL without time-gating, and no signal with time-gating. Permutation (ii) corresponded to the hybridization of TGT A-A647, which resulted in a mixture of QD and FRET$_2$-sensitized A647 PL in non-gated measurements, and no signal in time-gated measurements. The third permutation (iii) corresponded to the hybridization of TGT B-Tb, which yielded only QD PL without time-gating, and a mixture of Tb and FRET$_1$-sensitized QD PL with time-gating. Permutation (iv) corresponded to hybridization of both TGT A-A647 and TGT B-Tb. Here, the non-gated spectrum showed QD and FRET$_2$-sensitized A647 PL, whereas the time-gated spectrum showed Tb PL, FRET$_1$-sensitized QD PL and FRET$_2$-sensitized A647 PL, reflecting assembly of the full Tb-to-QD-to-A647 FRET relay.

The orthogonality of the two-plex hybridization assay was evaluated using an array of different mixtures of TGT A-A647 and TGT B-Tb, followed by calculation of the non-gated A647/QD PL ratio (FRET$_2$) and time-gated total QD+A647 PL sensitization (FRET$_1$) from the measured PL spectrum of each mixture. As the amount of TGT A-A647 increased, the non-gated A647/QD PL ratio increased linearly, but was relatively unaffected by the presence or absence of TGT B-Tb (FIG. 7B(i)). Similarly, as the amount of TGT B-Tb increased, the total QD+A647 PL sensitization increased linearly, but was minimally affected by changes in the presence of TGT A-A647 (FIG. 7B(ii)). The data in FIG. 7B(i-ii) were collected simultaneously in the same experiment and from the same samples. These results effectively demonstrated orthogonal quantitative responses, where the A647/QD PL ratio responded to TGT A-A647, and the total QD+A647 PL sensitization responded to TGT B-Tb. For a rigorous demonstration of the concept and analysis, the small amount of overlapping Tb PL were numerically deconvolved from the QD PL in the measured two-plex PL spectra (alternative analyses are discussed later). The LOD for TGT A-A647 and TGT B-Tb were estimated to be 17 nM (1.9 pmol) and 29 nM (3.2 pmol), respectively. The LOD thresholds were taken as three standard deviations above the average A647/QD PL ratio (0 nM TGT A-A647, 0-727 nM TGT B-Tb, time-gated) or total QD+A647 PL sensitization (0 nM TGT B-Tb, 0-454 nM TGT A-A647, non-gated). Despite the two-plex format, these LODs compare favorably to the time-gated, one-plex hybridization assay.

Due to the emission rate of the long lifetime FRET donor, the $FRET_1$ pathway is poorly observed promptly after interrogation (<100 ns), but readily observed over extended observation times ($10^5$-$10^6$ ns). This aids directly in distinguishing between the two FRET steps. The number and proximity of long lifetime FRET donors and fluorescent dyes assembled to the QD determines the rate of $FRET_1$ and $FRET_2$, respectively. Control over these parameters thus enables the modulation of $FRET_1$ and $FRET_2$, thereby permitting spectral-temporal encoding of information.

Applications

Potential applications areas utilizing luminescent probes or reporters in non-biological or biological applications requiring, or benefiting from, extending the observation window of FRET pair. Other applications include labeling, assays, or chemo/biosensing on the surface of or within cells, tissues (in vitro or in vivo), environmental samples, and/or other complex sample matrices prone to high levels of optical source scattering and/or autofluorescence that can be ameliorated by time-gating.

Potential applications also exist in areas where luminescent probes or reporters in biological applications requiring, or benefiting from, multiplexed detection in a spectro-temporal format. This includes: labeling, assays, or chemo/biosensing in vitro or within cells and tissues.

Further potential application areas are those where luminescence can be used for unique identification, tracking, or validation/authentication. This includes: optical barcodes for commercial/shipping use, and/or anti-counterfeit measures/forgery deterrent.

This technique may also be used advatageously in areas where traditional FRET has been employed, including measurements of binding and/or dissociation, enzymatic activity, protein folding, and cellular processes (such as endocytosis and protein synthesis).

Nanoparticles such as QDs also show great promise for a new generation of diagnostic probes, biomedical technologies, therapeutics, and single-vector combinations thereof, sometimes called "theranostics."

Advantages

QDs as intermediate acceptors/donors in FRET. Several properties of QDs are uniquely advantageous for assembling the two-step energy transfer relay, particularly when the QD is configured as an intermediary. The strong, broad QD absorption was resonant with the three strongest Tb emission lines and was characterized by extinction coefficients approaching an order of magnitude greater than that of most fluorescent dye acceptors (see ref. 45). The use of a fluorescent dye intermediary in the FRET relay configuration would also be hindered by a narrower absorption band that would only be resonant with two of the Tb emission lines. As a consequence, the QD acceptor offered a much larger spectral overlap integral and Förster distance with the Tb. The QD PL was also well separated from the Tb PL (except for the Tb emission line at 620 nm, which was the least intense of all the lines). In turn, when the QD functioned as the donor for the final A647 acceptor in the relay, the narrow QD PL provided strong overlap with the A647 absorption, while its peak remained spectrally well-resolved from the A647 emission at 675 nm. The latter would not have been possible with a fluorescent dye intermediary, given the characteristic broad and red-tailed dye emission profile.

The non-trivial surface area of the QD was of almost equal importance to its optical properties, and its utilization as a central nanoscaffold greatly facilitated the physical assembly of the energy transfer relay. In contrast, the use of a fluorescent dye intermediary in the relay would require an extrinsic scaffold, such as a protein or double-stranded DNA, to provide the necessary proximity with the initial donor(s) and final acceptor(s). Such a scaffold would not readily provide the approximately centrosymmetric distribution of Tb and A647 that was achieved with the QD intermediary, and which enabled straightforward analysis. Further, since the QD was its own intrinsic scaffold, it enabled the use of peptides and nucleic acids in a biological rather than structural motif. A maximum of 20 total peptides (PEP A+PEP B) were assembled per QD here, which is less than half of the maximum packing expected for even smaller QDs. This "extra" surface availability could allow the assembly of one or more other biomaterials to the QD in order to provide utility beyond the FRET relay. For example, cell penetrating or other targeting peptides could be added to induce cellular uptake or in vivo targeting of the final bioconjugate as described in refs. 46-51.

The properties of $His_6$ self-assembly for binding to the QD also provided advantages. Utilizing the $His_6$ motif offered simplicity, efficiency, and reproducibility. QD bioconjugation required only mixing of the QD and the desired equivalents of biomolecule(s). This level of control over QD-bioconjugate valence effectively permitted tuning of the relative efficiency of the $FRET_1$ and $FRET_2$ pathways, regardless of the use of Tb/A647 labeled $His_6$-appended peptides, or $His_6$-appended oligonucleotide probes hybridized with labeled target. Such versatile and incremental tuning of two distinct FRET pathways—solely through assembly valence—may be unique to the use of QDs and $His_6$-bioconjugation in these types of assemblies. In contrast, assembling biotinylated DNA to streptavidin-coated QDs results in a large amount of heterogeneity in separation distance, hindering control and characterization of FRET, as noted in ref. 34. Purely synthetic chemical approaches to deriving similar architectures based on, for example, a dendrimeric substrate, are extremely labor intensive, and neither spin coating nor layer-by-layer approaches would provide the same levels of control and/or precision as $His_6$ (see refs. 17 and 52).

Time-Gated Biosensing.

With few exceptions, multistep FRET relays incorporating QD-bioconjugates have been based on QD-to-dye-to-dye energy transfer configurations (see refs. 20-22). The role of the relay in these instances was primarily to extend the range of energy transfer and/or to allow for wavelength shifting. Herein, the former consideration was addressed by the large Förster distances of the $FRET_1$ (10.1 nm) and $FRET_2$ (7.5 nm) pairs, while the latter was addressed by pairing a red-emitting QD with the deeper-red A647 acceptor. The unique features of the Tb-to-QD-to-A647 FRET relay were the added ability to make time-gated QD PL measurements, and sensitization of QD-to-A647 energy transfer over a millisecond timescale. With time-gating, undesirable direct excitation of the final A647 acceptor—regardless of the excitation wavelength used—was avoided due to its ~1 ns fluorescence lifetime.

However, a potentially more important advantage arises from the <20 ns characteristic decay times of cellular and tissue autofluorescence (see ref. 56), such that the time-gating afforded by Tb-to-QD FRET is expected to permit the separation of analytical PL signals from unwanted background PL in almost any complex biological matrix. While the protease sensing demonstrated in this work was primarily proof-of-concept for demonstrating utility of the FRET relay, it should be noted that abnormal protease activity is associated with many diseases, including ischemia, autoimmune and neurodegenerative disease, as well as several types of cancers (see ref. 57). This relevance suggests, for example, the possibility of sensitive, time-gated, in situ measurements of protease activity associated with over-expressed extracellular matrix metalloproteinases in complex tumor milieu. Use in complex biological matrices will be predicated on the fidelity of the QD-conjugate assemblies therein. Complexation of the Tb is highly stable and selective for lanthanide ions, polyhistidine is not an endogenous motif, and PEG coatings are largely biocompatible—all of which suggest that preassembled QD-conjugates should remain functional in biological matrices.

In addition to the advantages of time-gating via the Tb-QD FRET pair, there are advantages associated with the ratiometric detection afforded by the QD-A647 FRET pair. Ratiometric analyses tend to be relatively insensitive to dilutions and small variations in excitation intensity or between different instruments. This format is also particularly well suited to assays in a kinetic format, where donor and acceptor PL intensities dynamically change over extended time periods (e.g. hours) and are highly susceptible to instrumental drift and noise.

Orthogonal Spectrotemporal Multiplexing.

Figure 7:
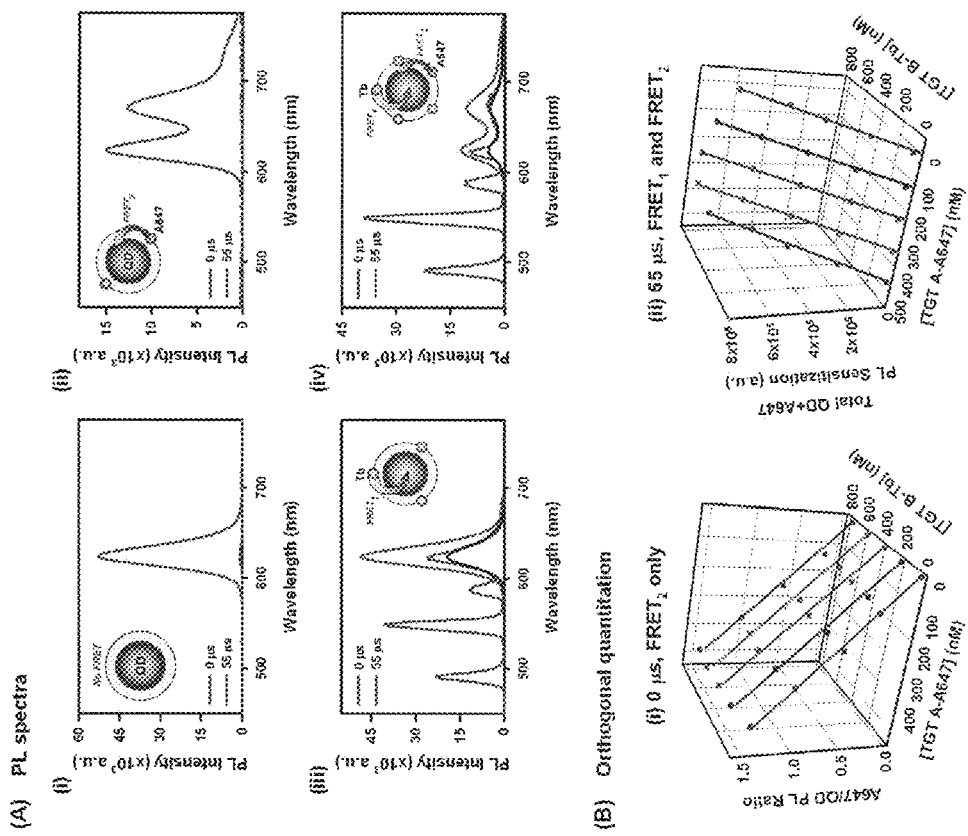
FIG. 7 shows time-gated two-plex sensing of nucleic acid hybridization using a two-step QD-FRET relay. (A) PL spectra showing the characteristic non-gated (~0 μs) and time-gated (55 μs) response of (PRB B)$_{16}$-QD-(PRB A)$_{10}$ assemblies: (i) no target; (ii) TGT A-A647; (iii) TGT B-Tb; and (iv) TGT A-A647 and TGT B-Tb. The solid black lines show scaling of the non-gated PL spectrum to fit the time-gated PL spectrum (via numerical deconvolution). (B) Orthogonal calibrations curves based on measurement of: (i) the non-gated A647/QD PL ratio, and (ii) time-gated total QD+A647 PL sensitization. Each parameter responded linearly to increasing amounts of the corresponding target, and was approximately independent of the other analytical parameter.

In previous FRET sensing configurations based on QD donors, multiplexed information has been encoded by using two different colors of QD with either a common or different FRET acceptors (refs. 60 and 35, respectively). Multiplexing configurations where QDs have been used as FRET acceptors also rely on multiple QD colors (refs. 11 and 14). In practice, ratiometric methods based on use of different fluorescent acceptor(s) have been preferred, and the number of colors measured (i.e. wavelength bands) was always greater than the number of targets. Moreover, multiplexing in these formats was usually limited to the ensemble since each individual QD-bioconjugate still only transduced one type of target. Compared to this state-of-the-art, the Tb-to-QD-to-A647 FRET relay offers an important and unique possibility in multiplexed bioanalysis: the ability to simultaneously transduce the activity of two different biomolecular targets by using a single color of QD in combination with orthogonal PL signals that are sensitive to different luminophores (the latter are bound to the QDs via biomolecular recognition). Furthermore, since these signals were proportional to the number of proximal acceptors, the viability of this assay format was demonstrated in a semi-quantitative, two-plex hybridization assay (FIG. 7).

The use of full PL spectra and numerical deconvolution to resolve overlapping Tb and QD PL was performed for characterization and validation of the two-plex strategy, and is not generally expected to be required in the majority of practical applications of the FRET relay assembly. The small degree of Tb crosstalk in measuring QD PL only appeared in the time-gated measurement and systematically added to the apparent magnitude of the latter, such that it was readily calibrated into quantitative results. Alternatively, the use of 605 nm PL QDs, which would also be a suitable intermediary for the Tb and A647 in a relay, could potentially avoid this limited crosstalk since its PL maximum falls between the 585 and 620 nm Tb emission lines. In either case, the Tb PL intensity need not factor into the analysis, thereby permitting the use of two-color detection centered on the QD and A647 PL. Importantly, this two-color advantage does not come at the cost of ratiometric measurements. Since the A647 and QD PL manifests in both the non-gated and time-gated PL spectra, the $FRET_1$ pathway can be measured relative to the directly excited $FRET_2$ pathway by dividing the time-gated A647+ QD PL sensitization ($FRET_1$ signal) by the non-gated A647+ QD PL, which is a reference state independent of $FRET_1$. Thus, both $FRET_1$ and $FRET_2$ can be analyzed ratiometrically. The caveat of this FRET-relay strategy is that only static biological processes, or those with slow dynamics ($\geq 10^{-2}$ s), can be monitored due to the need for microsecond time-gating and a millisecond integration time.

The orthogonal calibration curves in FIG. 7B are a powerful confirmation of the approximate independence of the $FRET_1$ and $FRET_2$ pathways, as well as the strong biosensing potential of this time-gated, multiplexed FRET configuration. Dependence on directly-labeled targets can be avoided by using labeled reporter oligonucleotides in a sandwich format (refs. 43, 61, and 62), intercalating dyes (refs. 35, 42, and 63), or molecular beacon configurations (refs. 29, 64, and 65). Simultaneous monitoring of two different proteases should also be feasible in this spectrotemporal format, as well as targeting of many other enzymatic processes (refs. 14 and 66). An intriguing idea is utilizing the $FRET_1$ and $FRET_2$ processes to monitor and correlate physically-associated, coupled, or cascaded events while still using a single QD assembly. For example, certain proteases have differential sensitivity to phosphorylated versus non-phosphorylated peptide substrates. This capability could allow the correlation of kinase/phosphatase activity that is coupled to subsequent proteolysis. Beyond in vitro applicability, access to multiplexed sensing using a single compact QD-based probe can reduce the amount of extraneous material that must be delivered intracellularly. This feature potentially lessens the perturbation of a cellular system under study, and/or avoids challenges associated with differences in the cellular delivery efficiency between two distinct probes. It would also reduce some optical complexity in multiplexed microscopy systems (e.g. four color channels for two distinct donor-acceptor pairs without a relay, vs. two color channels and electronics for time-gating when utilizing such a relay).

The advantages of the techniques described herein include the following:

1. The use of a long-lifetime (microsecond to millisecond) initial donor for $FRET_1$ enables time-gated observation, with good fidelity, of an (approximately) independent $FRET_2$ process (intermediary-terminal acceptor pair), which would otherwise only be visible with prompt observation. Time-gated observation allows for the collection and accumulation of large amounts of data, with improved signal-to-noise with weak signals, and can be useful in situations when multiple events might contribute to the same signal.

2. The time-gated observation window that is suitable for the amelioration of scattered source light and sample/matrix autofluorescence such as that found in biological samples and in vivo cellular and tissue formats.

3. The $FRET_2$ pair can be spectrally observed at their characteristic wavelengths in both prompt and time-gated observation after pulse/flash excitation.

4. The two-step FRET relay is a discrete entity (compared with multiple one-step FRET pairs).

5. Approximately independent tuning of $FRET_1$ and $FRET_2$ by controlling the number of initial donors and terminal acceptors, respectively, in association with the intermediary acceptor/donor.

6. Approximately independent tuning of $FRET_1$ and $FRET_2$ by controlling the proximity between the intermediary acceptor/donor and the initial donor(s) and terminal acceptor(s), respectively.

7. Three-fold flexibility in tuning the $FRET_1$ and $FRET_2$ efficiencies by the selection of the initial donor, intermediary acceptor/donor, and/or terminal acceptor on the basis of spectral overlap.

8. The two-step FRET relay requires less spectral bandwidth and/or channels to encode, for example, two-plex information when compared to two discrete FRET pairs.

9. Spectro-temporal information is more difficult to replicate than solely spectral information (e.g. as an authenticator/forgery deterrent).

10. The two-step FRET relay can potentially be used in solution, at an interface, within cellular environments, or embedded within matrices such as host nanoparticles or polymeric films/coatings.

11. Applicability and compatibility with both biological and non-biological environments.

12. Beyond the long lifetime FRET donor- or dye-labeled peptide and oligonucleotide assembly to QDs demonstrated herein, two-step FRET relays can be comprised of fluorescent dyes and long lifetime FRET donors labeled/conjugated to a variety of other biomolecules, organic, or inorganic scaffolds that assemble to, or incorporate, a suitable intermediary acceptor/donor.

REFERENCES (1) Algar, W. R.; Susumu, K.; Delehanty, J. B.; Medintz, I. L. *Anal. Chem.* 2011, 83, 8826-8837.
(2) Rosenthal, S. J.; Chang, J. C.; Kovtun, O.; McBride, J. R.; Tomlinson, I. D. *Chem. Biol.* 2011, 18, 10-24.
(3) Gill, R.; Zayats, M.; Willner, I. *Angew. Chem. Int. Ed.* 2008, 47, 7602-7625.
(4) Hildebrandt, N. *ACS Nano* 2011, 5, 5286-5290.
(5) Medintz, I. L.; Mattoussi, H. *Phys. Chem. Chem. Phys.* 2009, 11, 17-45.
(6) Nabiev, I.; Rakovich, A.; Sukhanova, A.; Lukashev, E.; Zagidullin, V.; Pachenko, V.; Rakovich, Y. P.; Donegan, J. F.; Rubin, A. B.; Govorov, A. O. *Angew. Chem. Int. Ed.* 2010, 49, 7217-7221.
(7) Algar, W. R.; Tavares, A. J.; Krull, U. J. *Anal. Chim. Acta* 2010, 673, 1-25.
(8) Clapp, A. R.; Medintz, I. L.; Fisher, B. R.; Anderson, G. P.; Mattoussi, H. *J. Am. Chem. Soc.* 2005, 127, 1242-1250.
(9) Hildebrandt, N.; Charbonnière, L. J.; Beck, M.; Ziessel, R. F.; Löhmannsröben, H. G. *Angew. Chem. Int. Ed.* 2005, 44, 7612-7615.
(10) Charbonnière, L. J.; Hildebrandt, N.; Ziessel, R. F.; Löhmannsröben, H. G. *J. Am. Chem. Soc.* 2006, 128, 12800-12809.
(11) Geißler, D.; Charbonnière, L. J.; Ziessel, R. F.; Butlin, N. G.; Löhmannsröben, H. G.; Hildebrandt, N. *Angew. Chem. Int. Ed.* 2010, 49, 1396-1401.
(12) Morgner, F.; Geißler, D.; Stufler, S.; Butlin, N. G.; Löhmannsröben, H. G.; Hildebrandt, N. *Angew. Chem. Int. Ed.* 2010, 49, 7570-7574.
(13) So, M. K.; Xu, C. J.; Loening, A. M.; Gambhir, S. S.; Rao, J. H. *Nat. Biotechnol.* 2006, 24, 339-343.
(14) Xia, Z. Y.; Xing, Y.; So, M. K.; Koh, A. L.; Sinclair, R.; Rao, J. H. *Anal. Chem.* 2008, 80, 8649-8655.
(15) Liu, X.; Freeman, R.; Golub, E.; Willner, I. *ACS Nano* 2011, 5, 7648-7655.
(16) Freeman, R.; Liu, X. Q.; Willner, I. *J. Am. Chem. Soc.* 2011, 133, 11597-11604.
(17) Seker, U. O. S.; Ozel, T.; Demir, H. V. *Nano Lett.* 2011, 11, 1530-1539.
(18) Achermann, M.; Jong, S.; Balet, L.; Montano, G. A.; Hollingsworth, J. A. *ACS Nano* 2011, 5, 1761-1768.
(19) Feng, C. L.; Zhong, X. H.; Steinhart, M.; Caminade, A. M.; Majoral, J. P.; Knoll, W. *Small* 2008, 4, 566-571.
(20) Medintz, I. L.; Clapp, A. R.; Mattoussi, H.; Goldman, E. R.; Fisher, B.; Mauro, J. M. *Nat. Mater.* 2003, 2.
(21) Geissbuehler, I.; Hovius, R.; Martinez, K. L.; Adrian, M.; Thampi, K. R.; Vogel, H. *Angew. Chem. Int. Ed.* 2005, 44, 1388-1392.
(22) Lu, H.; Schops, O.; Woggon, U.; Niemeyer, C. M. *J. Am. Chem. Soc.* 2008, 130, 4815-4827.
(23) Boeneman, K.; Prasuhn, D. E.; Blanco-Canosa, J. B.; Dawson, P. E.; Melinger, J. S.; Ancona, M.; Stewart, M. H.; Susumu, K.; Huston, A.; Medintz, I. L. *J. Am. Chem. Soc.* 2010, 132, 18177-18190.
(24) Mei, B. C.; Susumu, K.; Medintz, I. L.; Delehanty, J. B.; Mountziaris, T. J.; Mattoussi, H. *J. Mater. Chem.* 2008, 18, 4949-4958.
(25) Mei, B. C.; Susumu, K.; Medintz, I. L.; Mattoussi, H. *Nat. Protocols* 2009, 4, 412-423.
(26) Schnolzer, M.; Alewood, P.; Jones, A.; Alewood, D.; Kent, S. B. H. *Int. J. Pep. Prot. Res.* 1992, 40, 180-193.
(27) Prasuhn, D. E.; Feltz, A.; Blanco-Canosa, J. B.; Susumu, K.; Stewart, M. H.; Mei, B. C.; Yakovlev, A. V.; Loukou, C.; Mallet, J. M.; Oheim, M.; Dawson, P. E.; Medintz, I. L. *ACS Nano* 2010, 4, 5487-5497.
(28) Xu, J.; Corneillie, T. M.; Moore, E. G.; Law, G. L.; Butlin, N. G.; Raymond, K. N. *J. Am. Chem. Soc.* 2011, DOI: 10.1021/ja2079898.
(29) Medintz, I. L.; Berti, L.; Pons, T.; Grimes, A. F.; English, D. S.; Alessandrini, A.; Facci, P.; Mattoussi, H. *Nano Lett.* 2007, 7, 1741-1748.
(30) Dennis, A. M.; Sotto, D. C.; Mei, B. C.; Medintz, I. L.; Mattoussi, H.; Bao, G. *Bioconj. Chem.* 2010, 21, 1160-1170.
(31) Sapsford, K. E.; Pons, T.; Medintz, I. L.; Higashiya, S.; Brunel, F. M.; Dawson, P. E.; Mattoussi, H. *J. Phys. Chem. C* 2007, 111, 11528-11538.
(32) Prasuhn, D. E.; Deschamps, J. R.; Susumu, K.; Stewart, M. H.; Boeneman, K.; Blanco-Canosa, J. B.; Dawson, P. E.; Medintz, I. L. *Small* 2010, 6, 555-564.
(33) Charbonnière, L. J.; Hildebrandt, N. *Eur. J. Inorg. Chem.* 2008, 21, 3241-3251.
(34) Boeneman, K.; Deschamps, J. R.; Buckhout-White, S.; Prasuhn, D. E.; Blanco-Canosa, J. B.; Dawson, P. E.; Stewart, M. H.; Susumu, K.; Goldman, E. R.; Ancona, M.; Medintz, I. L. *ACS Nano* 2010, 4, 7253-7266.
(35) Algar, W. R.; Krull, U. J. *Anal. Chim. Acta* 2007, 581, 193-201.
(36) Boeneman, K.; Mei, B. C.; Dennis, A. M.; Bao, G.; Deschamps, J. R.; Mattoussi, H.; Medintz, I. L. *J. Am. Chem. Soc.* 2009, 131, 3828-3829.
(37) Clapp, A. R.; Medintz, I. L.; Mauro, J. M.; Fisher, B. R.; Bawendi, M. G.; Mattoussi, H. *J. Am. Chem. Soc.* 2004, 126, 301-310.
(38) Medintz, I. L.; Clapp, A. R.; Brunel, F. M.; Tiefenbrunn, T.; Uyea, H. T.; Chang, E. L.; Deschamps, J. R.; Dawson, P. E.; Mattoussi, H. *Nat. Mater.* 2006, 5, 581-589.
(39) Shi, Z. S.; Olson, C. A.; Bell, A. J.; Kallenbach, R. N. *Biopolymers* 2001, 60, 366-380.

(40) Sapsford, K. E.; Granek, J.; Deschamps, J. R.; Boeneman, K.; Blanco-Canosa, J. B.; Dawson, P. E.; Susumu, K.; Stewart, M. H.; Medintz, I. L. *ACS Nano* 2011, 5, 2687-2699.
(41) Sapsford, K. E.; Farrell, D.; Sun, S.; Rasooly, A.; Mattoussi, H.; Medintz, I. L. *Sens. Act. B* 2009, 139, 13-21.
(42) Zhou, D.; Ying, L.; Hong, X.; Hall, E. A.; Abell, C.; Klenerman, D. *Langmuir* 2008, 24, 1659-1664.
(43) Algar, W. R.; Krull, U. J. *Anal. Chem.* 2009, 81, 4113-4120.
(44) Algar, W. R.; Krull, U. J. *Anal. Bioanal. Chem.* 2010, 398, 2439-2449.
(45) Resch-Genger, U.; Grabolle, M.; Cavaliere-Jaricot, S.; Nitschke, R.; Nann, T. *Nat. Methods* 2008, 5, 763-775.
(46) Prasuhn, D. E.; Blanco-Canosa, J. B.; Vora, G. J.; Delehanty, J. B.; Susumu, K.; Mei, B. C.; Dawson, P. E.; Medintz, I. L. *ACS Nano* 2010, 4, 267-278.
(47) Delehanty, J. B.; Medintz, I. L.; Pons, T.; Brunel, F. M.; Dawson, P. E.; Mattoussi, H. *Bioconj. Chem.* 2006, 17, 920-927.
(48) Medintz, I. L.; Pons, T.; Delehanty, J. B.; Susumu, K.; Brunel, F. M.; Dawson, P. E.; Mattoussi, H. *Bioconj. Chem.* 2008, 19, 1785-1795.
(49) Akerman, M. E.; Chan, W. C. W.; Laakkonen, P.; Bhatia, S. N.; Ruoslahti, E. *Proc. Natl. Acad. Sci. USA* 2002, 99, 12617-12621.
(50) Derfus, A. M.; Chan, W. C. W.; Bhatia, S. N. *Adv. Mater.* 2004, 16, 961-966.
(51) Ruan, G.; Agrawal, A.; Marcus, A. I.; Nie, S. *J. Am. Chem. Soc.* 2007, 129, 14759-14766.
(52) Walker, B. J.; Bulovic, V.; Bawendi, M. G. *Nano Lett.* 2010, 10, 3995-3999.
(53) Pons, T.; Medintz, I. L.; Wang, X.; English, D. S.; Mattoussi, H. *J. Am. Chem. Soc.* 2006, 128, 15324-15331.
(54) Xiao, M.; Selvin, P. R. *J. Am. Chem. Soc.* 2001, 123, 7067-7073.
(55) Algar, W. R.; Krull, U. J. *Sensors* 2011, 11, 6214-6236.
(56) Bachmann, L.; Zezell, D. M.; Ribeiro, A.d. C.; Gomes, L.; Ito, A. S. *Appl. Spectrosc.* 2006, 41, 575-590.
(57) Elmore, S. *Toxicol. Pathol.* 2007, 35, 495-516.
(58) Liu, W.; Howarth, M.; Greytak, A. B.; Zheng, Y.; Nocera, D. G.; Ting, A. Y.; Bawendi, M. G. *J. Am. Chem. Soc.* 2008, 130, 1274-1284.
(59) Yu, W. W.; Chang, E.; Falkner, J. C.; Zhang, J.; Al-Somali, A. M.; Sayes, C. M.; Johns, J.; Drezek, R.; Colvin, V. L. *J. Am. Chem. Soc.* 2007, 129, 2871-2879.
(60) Clapp, A. R.; Medintz, I. L.; Uyeda, H. T.; Fisher, B. R.; Goldman, E. R.; Bawendi, M. G.; Mattoussi, H. *J. Am. Chem. Soc.* 2005, 127, 18212-18221.
(61) Zhang, C. Y.; Hu, *J. Anal. Chem.* 2010, 82, 1921-1927.
(62) Zhang, C. Y.; Yeh, H. C.; Kuroki, M. T.; Wang, T. H. *Nat. Mater.* 2005, 4, 826-831.
(63) Lim, T. C.; Bailey, V. J.; Ho, Y. P.; Wang, T. H. *Nanotechnol.* 2008, 19, 075701.
(64) Kim, J. H.; Morikis, D.; Ozkan, M. *Sens. Act. B* 2004, 102, 315-319.
(65) Cady, N. C.; Strickland, A. D.; Batt, C. A. *Mol. Cell. Probes* 2007, 21, 116-124.
(66) Kim, Y. P.; Oh, Y. H.; Oh, E.; Ko, S.; Han, M. K.; Kim, H. S. *Anal. Chem.* 2008, 80, 4634-4641.
(67) Rodems, S. M.; Hamman, B. D.; Lin, C.; Zhao, J.; Shah, S.; Heidary, D.; Makings, L.; Stack, J. H.; Pollok, B. A. *Assay Drug Devel. Technol.* 2002, 1, 9-19.

CONCLUDING REMARKS

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith

---

What is claimed is:

1. A FRET relay assembly comprising:

a long lifetime FRET donot, a semiconductor quantum dot (QD) configured as an intermediate acceptor/donor in FRET and assembled to the long lifetime FRET donor in sufficient proximity thereto so as to allow for a first FRET process between them, and a fluorescent dye configured as a terminal FRET acceptor and assembled to the QD in sufficient proximity thereto so as to allow for a second FRET process between them, wherein the long lifetime FRET donor has an excited state lifetime of at least one microsecond and the QD and fluorescent dye each have excited state lifetimes of less than 100 nanoseconds.

2. The FRET relay assembly of claim 1, wherein the long lifetime FRET donor comprises $Tb^{3+}$, $Eu^{3+}$, $Sm^{3+}$, $Tm^{3+}$, $Ru^{2+}$, or a combination thereof.

3. The FRET relay assembly of claim 1, wherein said long lifetime FRET donor and/or said fluorescent dye are bound to said QD using peptides, and/or oligonucleotides.

4. The FRET relay assembly of claim 1, wherein at least one $His_6$ motif is adapted to bind said long lifetime FRET donor and/or said fluorescent dye to said QD.

5. The FRET relay assembly of claim 1, wherein the QD is functionalized with carboxylate, amine, or poly(ethylene glycol).

6. The FRET relay assembly of claim 1, wherein the QD comprises ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, or InSb.

7. A population of quantum dots comprising:
a plurality of FRET relay assemblies according to claim 1 wherein said intermediate acceptor/donor QDs are of a single color and
additional QDs of the same color as the QD in the FRET relay assembly, bound to only one of said initial FRET donor or said terminal FRET acceptor.

* * * * *